(12) United States Patent
Palczewski et al.

(10) Patent No.: US 11,793,853 B2
(45) Date of Patent: *Oct. 24, 2023

(54) RETINYLAMINE DERIVITIVES FOR TREATMENT OF OCULAR DISORDERS

(71) Applicant: CASE WESTERN RESERVE UNIVERSITY, Cleveland, OH (US)

(72) Inventors: Krzysztof Palczewski, Cleveland, OH (US); Zheng-Rong Lu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 58 days.

This patent is subject to a terminal disclaimer.

(21) Appl. No.: 16/681,485

(22) Filed: Nov. 12, 2019

(65) Prior Publication Data

US 2020/0121754 A1 Apr. 23, 2020

Related U.S. Application Data

(63) Continuation of application No. 15/315,207, filed as application No. PCT/US2015/033585 on Jun. 1, 2015, now Pat. No. 10,471,118.

(60) Provisional application No. 62/005,158, filed on May 30, 2014.

(51) Int. Cl.
| | |
|---|---|
| A61K 38/05 | (2006.01) |
| A61K 31/16 | (2006.01) |
| A61K 47/60 | (2017.01) |
| A61K 47/65 | (2017.01) |
| A61K 9/00 | (2006.01) |
| A61K 31/165 | (2006.01) |
| A61K 31/40 | (2006.01) |

(52) U.S. Cl.
CPC ............ *A61K 38/05* (2013.01); *A61K 9/0053* (2013.01); *A61K 31/16* (2013.01); *A61K 31/165* (2013.01); *A61K 31/40* (2013.01); *A61K 47/60* (2017.08); *A61K 47/65* (2017.08)

(58) Field of Classification Search
None
See application file for complete search history.

(56) References Cited

U.S. PATENT DOCUMENTS

| | | | |
|---|---|---|---|
| 5,622,718 | A | 4/1997 | Al-Shamkhani et al. |
| 5,700,848 | A | 12/1997 | Soon-Shong et al. |
| 6,472,506 | B1 | 10/2002 | Moreau et al. |
| 10,471,118 | B2 * | 11/2019 | Palczewski .......... A61K 31/165 |
| 2003/0161791 | A1 | 8/2003 | Bentley et al. |
| 2004/0028745 | A1 | 2/2004 | Bouhadir et al. |
| 2005/0271705 | A1 | 12/2005 | Hughes et al. |
| 2008/0221208 | A1 | 9/2008 | Palczewski et al. |
| 2008/0275134 | A1* | 11/2008 | Palczewski ............ A61K 31/07 |
| | | | 514/725 |
| 2009/0197967 | A1* | 8/2009 | Kubota .................... A61P 27/02 |
| | | | 514/646 |
| 2010/0035986 | A1 | 2/2010 | Maeda et al. |
| 2010/0298443 | A1* | 11/2010 | Widder .................. A61K 31/16 |
| | | | 514/613 |
| 2011/0288170 | A1 | 11/2011 | Palczewski et al. |
| 2012/0014904 | A1* | 1/2012 | David .................... A61K 47/65 |
| | | | 424/78.3 |
| 2012/0093723 | A1* | 4/2012 | Sinko ..................... A61K 47/42 |
| | | | 424/1.69 |

FOREIGN PATENT DOCUMENTS

| | | |
|---|---|---|
| CN | 101745119 A | 6/2010 |
| EP | 3223016 A1 | 9/2017 |
| GB | 1334980 A | 10/1973 |
| WO | 2005/046575 A2 | 5/2005 |

OTHER PUBLICATIONS

Zonghua Liu, et al.; "Polysaccharides-based nanoparticles as drug delivery systems"; Advanced Drug Delivery Reviews; Journal; www.elsevier.com/locate/addr; Sep. 17, 2008; 13 pgs.
Applicant: Case Western Reserve University; "International Search Report and Written Opinion"; International PCT Application No. PCT/US2012/066847; International Filing Date: Nov. 28, 2012; dated Mar. 18, 2013; 13 pgs.
Applicant: Case Western Reserve University; International Application No. 19211484.1; Filing Date: Nov. 26, 2019; European Search Report; Date of Completion: May 27, 2020; 11 pgs.
Yujin Sun, et al.: "MRI of Breast Tumor Initiating Cells Using the Extra Comain-B of Fibronectin Targeting Nanoparticles", Theranostics, vol. 4, No. 8, Jan. 1, 2014, pp. 845-857, XP055432454, au issn: 1838-7460, doi: 10.7150/thno.8343.
Wang, Wei, et al.: "Screening and identifying of homing peptides to bladder cancer BIU-87 cells in Chinese", Chin. J. Cancer Biother., vol. 20, No. 5, Oct. 2013, pp. 515-521, XP002776454, abstract; figures 2-3.
Zheng Han, et al.: "EDB Fribronectin Specific Peptide for Prostate Cancer Targeting", Bioconjugate Chemistry, vol. 26, No. 5, May 20, 2015, pp. 830-838, XP055432466, ISSN: 1043-1802, DOI: 10.1021/acs.bioconjchem.5b00178.

(Continued)

*Primary Examiner* — Maury A Audet
(74) *Attorney, Agent, or Firm* — TAROLLI, SUNDHEIM, COVELL & TUMMINO, LLP

(57) ABSTRACT

A pharmaceutical composition includes a retinylamine derivative having the following formula:

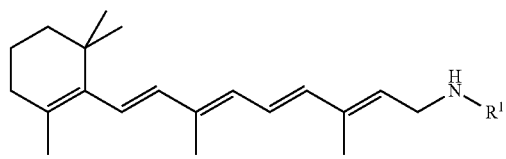

where $R^1$ is an amino acid residue, a dipeptide or a tripeptide that is linked to the retinylamine by an amide bond.

6 Claims, 10 Drawing Sheets

(56) References Cited

OTHER PUBLICATIONS

Zheng Han et al.: "An EDB fibronectin specific contrast agent for molecular imaging of cancer metastasis" 23rd Annual Meeting & Exhibition 30 May-Jun. 2015, Proc. Intl. Soc. Mag. Reson. Med., vol. 23, Jun. 3, 2015, XP009502183, Retrieved from the Internet: URL: http://dev.ismrm.org/2015/1910.html [retrieved on Dec. 6, 2015].

* cited by examiner

Figs. 7A-D (***, $p < 0.001$, Ret-NH$_2$ VS Ret-L-Val-Gly and Ret-L-Phe)

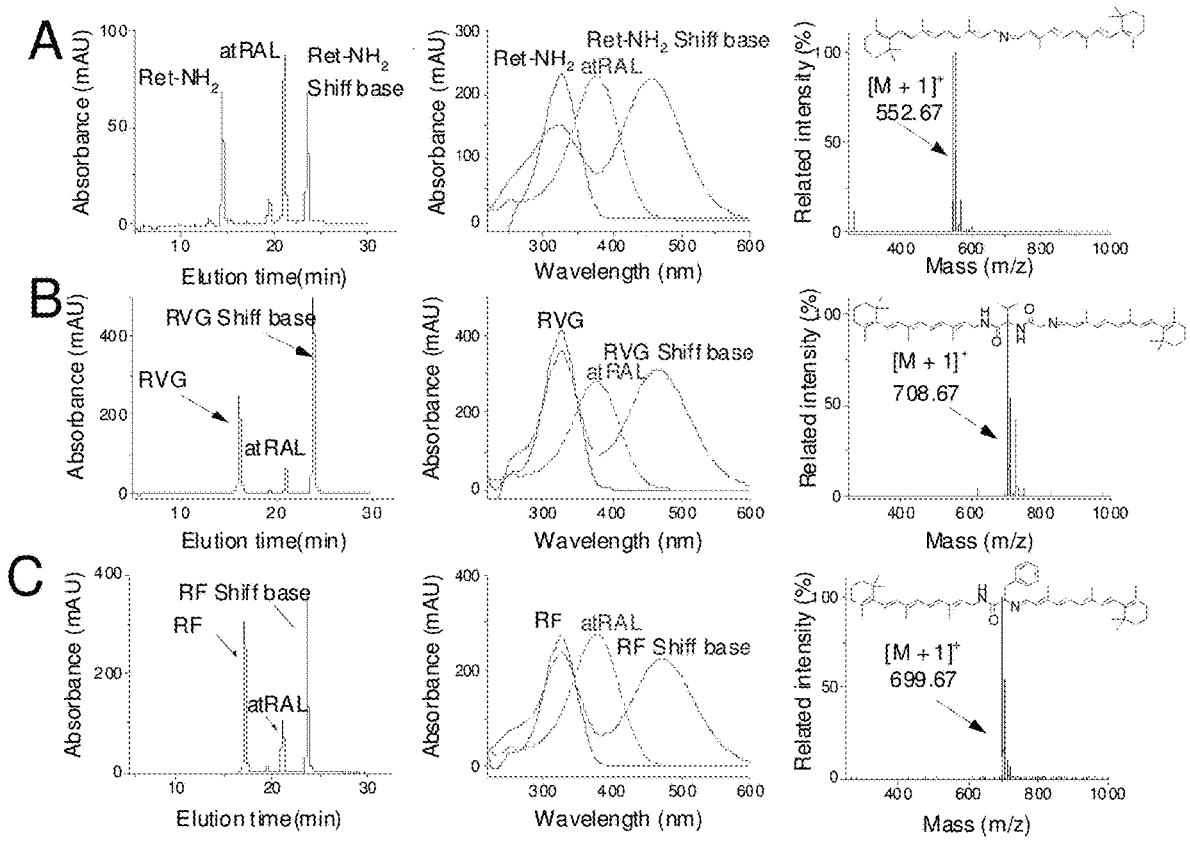
Figs. 13A-C

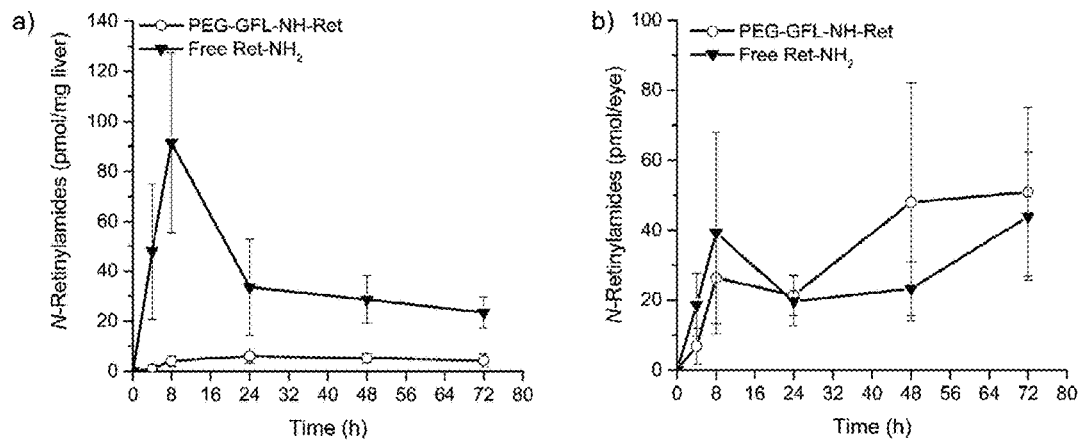
Figs. 14A-B
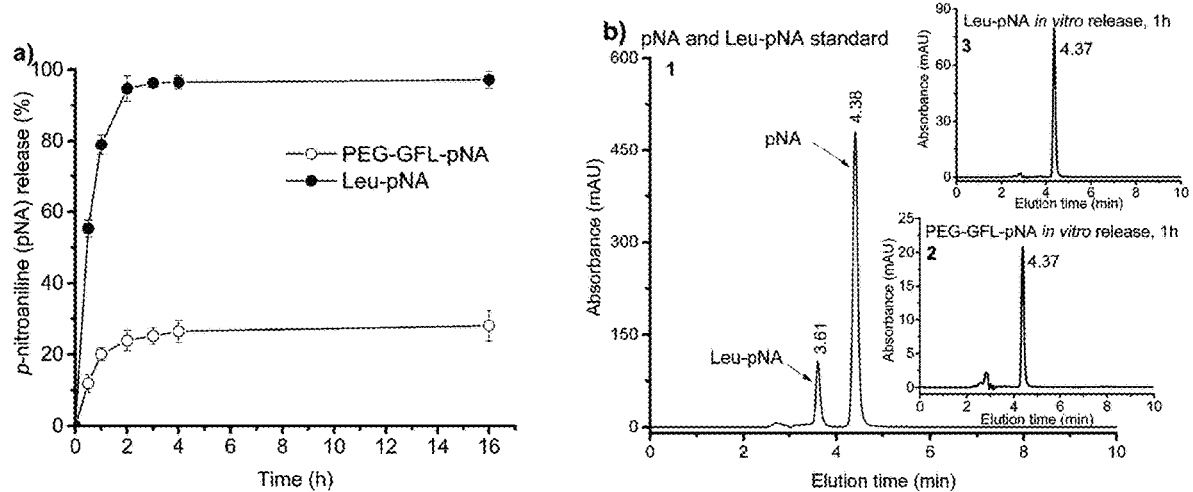
Figs. 15A-B

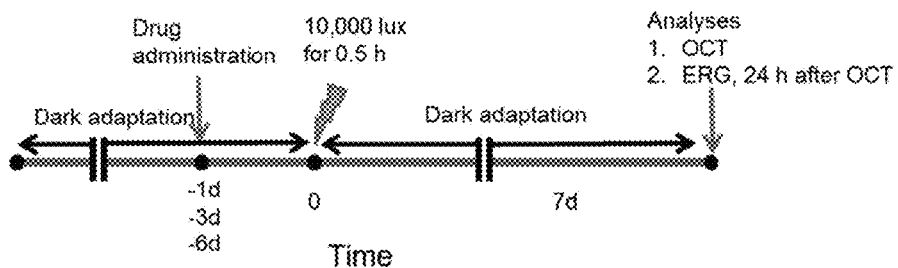
Fig. 16
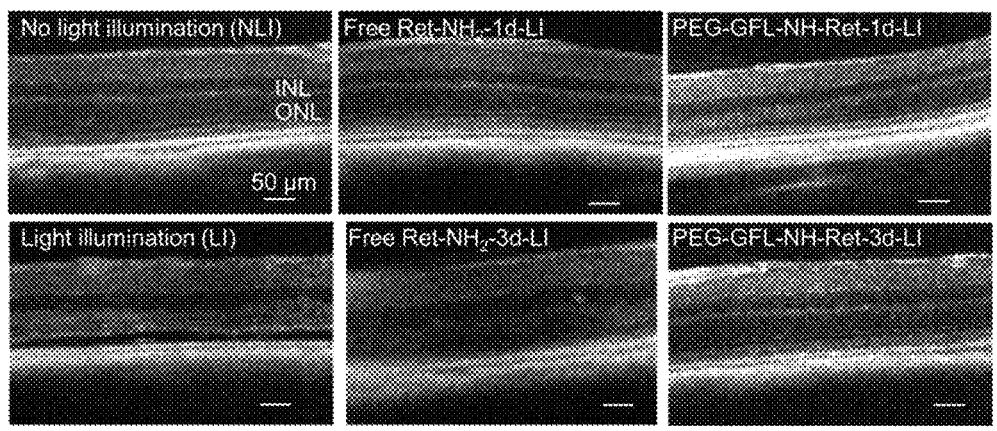
Fig. 17
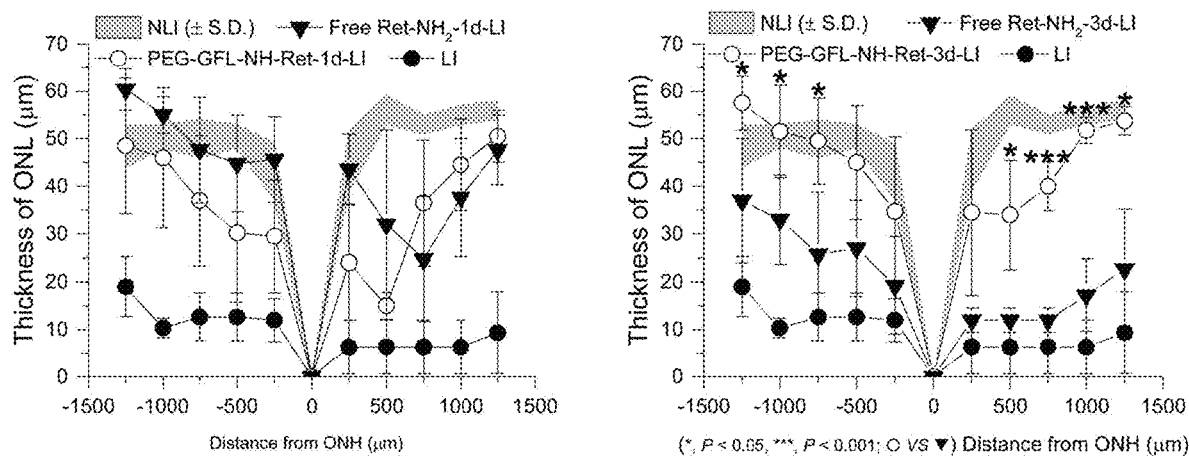
Figs. 18A-B

RETINYLAMINE DERIVITIVES FOR TREATMENT OF OCULAR DISORDERS

RELATED APPLICATION

This application claims priority from U.S. Provisional Application No. 62/005,158, filed May 30, 2014, the subject matter of which is incorporated herein by reference in its entirety.

GOVERNMENT FUNDING

This invention was made with government support under EY021126 awarded by the National Institutes of Health. The government has certain rights in the invention.

BACKGROUND

Vertebrate vision, initiated by photoisomerization of the chromophore 11-cis-retinal to all-trans-retinal (atRAL) in the retina, is maintained by continuous regeneration of 11-cis-retinal through a complex enzymatic pathway known as the retinoid (visual) cycle. If the conversion or clearance of atRAL in the photoreceptor cells is disrupted, this reactive aldehyde can form toxic dimeric condensation products, including N-retinyl-N-retinylidene-ethanolamine (A2E) and A2E-like derivatives. These toxic products contribute to retinal degenerative diseases, such as Stargardt disease (STGD) and age-related macular degeneration (AMD). Thus, excessive production and slow transformation of toxic atRAL are considered as one of the key factors in initiating retinal degeneration characterized by progressive photoreceptor cell death induced by both acute and chronic light exposure.

To date, there is no effective treatment that prevents, halts, or slows down the progression of STGD, AMD, and other retinal degenerative diseases in humans. However, it has been reported that, sequestration of atRAL can reduce the accumulation of A2E-like derivatives, prevent retinal degeneration and preserve vision in animal models, and potentially in humans.

Retinylamine (Ret-$NH_2$) is an aldehyde scavenger and an inhibitor of RPE65, a critical isomerase of the retinoid cycle. Ret-$NH_2$ also can effectively reduce levels of free atRAL in the retinas of other animal models and holds great promise as a therapeutic agent to prevent acute light induced retinal degeneration. However, this compound has various shortcomings that limit its clinical utility.

SUMMARY

Embodiments described herein relate to pharmaceutical compositions that include retinylamine derivatives and to their use in treating ocular disorders in subjects in need thereof. Disruptions in the conversion or clearance of all-trans-retinal (atRAL) in the retinoid cycle chemistry can lead to the accumulation of toxic at RAL, which is considered one of the key factors known to initiate progressive retinal dystrophy. Retinylamine and its analogues are known to be effective in lowering the concentration of atRAL within the retina and thus prevent retina degeneration in mouse models of human retinopathies.

It was found that retinylamine can be chemically modified with amino acids and peptides to improve the stability and ocular bioavailability of the therapeutics and to minimize its side effects.

In some embodiments, the retinylamine derivatives formed by chemical modification with amino acids and peptides to improve their stability and ocular bioavailability and minimize their side effects can have the following formula:

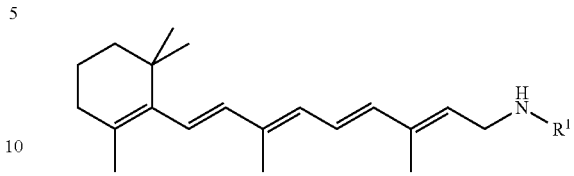

where $R^1$ is an amino acid residue, a dipeptide or a tripeptide that is linked to the retinylamine by an amide bond.

In some embodiments, $R^1$ can include at least one of L-phenylalanine, L-leucine, L-isoleucine, L-alanine, L-proline, L-valine, glycine, β-alanine, D-alanine, or D-valine. For example, $R^1$ can be selected from the group consisting of L-phenylalanine, L-leucine, L-isoleucine, L-alanine, L-proline, L-valine, glycine, β-alanine, D-alanine, D-valine, glycine-glycine, L-valine-glycine, and glycine-L-valine.

In other embodiments, $R^1$ can include at least one of L-valine or glycine. Examples of retinylamine derivatives in which $R^1$ can include at least one of L-valine or glycine are glycine, L-valine-glycine, and glycine-L-valine.

In some embodiments, the retinylamine derivative can have at least one of the following properties compared to retinylamine, when administered alone: enhanced gastrointestinal absorption; enhanced generation of 11-cis-retinol; or reduced inhibition of RPE65 isomerase activity.

In still other embodiments, the composition can include a biocompatible polymer linked to the retinylamine derivative with an oligopeptide spacer. The oligopeptide spacer can be degradable by intestinal enzymes during digestion of the composition to provide delayed, and/or sustained delivery of the retinylamine derivative upon enteral administration of the composition to a subject.

In some embodiments, the retinylamine derivatives can be administered to a subject by enteral or oral administration to treat an ocular disorder in a subject associated with light induced retinal degeneration and/or aberrant all-trans-retinal clearance in the retina. The ocular disorder can include, for example, retinal disorders, such as retinal degeneration, geographic atrophy (GA), macular degeneration, including age-related macular degeneration, Stargardt disease, and retinitis pigmentosa.

BRIEF DESCRIPTION OF THE DRAWINGS

FIGS. 13(A-C) illustrate plots showing the identification of the all-trap-retinal Shiff base. Incubate retinylamine derivatives RVG and RF (0.2 mM) with all-trans-retinal in ethanol 2 h at room temperature, then analyzed by HPLC and LC-MS, the schiff base was detected at 460 nm. HPLC spectrum of Schiff base reaction. The corresponding UV-vis spectra of reaction materials and their Schiff base. Mass spectra of their corresponding protonated Schiff base.

FIGS. 14 (A-B) illustrate plots showing pharmacokinetic distribution of N-retinylamides, the main metabolites of Ret-NH2, in the liver (a) and eye (b) after oral administration of Ret-NH2 and PEG-GFL-NH-Ret. The formulated conjugate, PEG-GFL-NH-Ret or Ret-NH2 (1 mg equivalent of Ret-NH2/mouse), was orally gavaged into dark-adapted 4-week-old C57BL wild-type female mice. Mice then were sacrificed at predetermined time points (4, 12, 24, 48, 72, 96, 120 h) after such treatment. N-Retinylamides were extracted from the eyes and liver and quantitatively determined by HPLC. Error bars indicate SD of the means (n=6).

FIGS. 15 (A-B) illustrate plots showing In vitro drug release kinetics of the conjugate PEG-GFL-pNA. (a) Release kinetics of pNA from PEG-GFL-pNA and Leu-pNA in the homogenates of rat intestinal brush border in isotonic phosphate buffer at pH 6.8 assayed by HPLC; (b) representative HPLC spectra of the released products: (1) pNA and Leu-pNA standard, (2) PEG-GFL-pNA in vitro release at 1 h, (3) Leu-pNA in vitro release at 1 h. HPLC conditions: analytical C18 reverse column (250 mm×4.6 mm, i.d., 5 µm particle size) with a mobile phase of H2O/actonitrile (40:60, v/v) with 0.05% trifluoroacetic acid, flow rate of 1.0 mL/min and UV detector set at 375 nm.

FIG. 16 illustrates a schematic representation of the experimental design for assessing the effectiveness of the conjugate. After 4-week-old female Abca4-/-Rdh8-/- mice were kept in the dark for 48 h, they were given either free Ret-NH2 or conjugate PEG-GFL-NH-Ret by gastric gavage at an equivalent dose of 0.5 mg Ret-NH2 per mouse. Mouse eyes were illuminated with 10000 lux light for 30 min either 1 day (1 d), 3 days (3 d), or 6 days (6 d) after the gavage. Mice then were kept in the dark for 7 days, after which final retinal evaluations were performed.

FIG. 17 illustrates OCT images of Abca4$^{-/-}$Rdh8$^{-/-}$ mouse retinas in different treatment groups (NLI=no light illumination; LI=light illuminated). Scale bar indicates 50 µm in the OCT image.

FIGS. 18(A-B) illustrate plots showing the ONL thickness measured from in vivo OCT images obtained along the vertical meridian from the superior to inferior retina of mice gavaged either 1 day (c) or 3 days (d) before bright light exposure. Statistical analysis was performed to compare the treatment groups using one-way ANOVA. Error bars indicate SD of the means (n=4-5).

DETAILED DESCRIPTION

Figure 1:
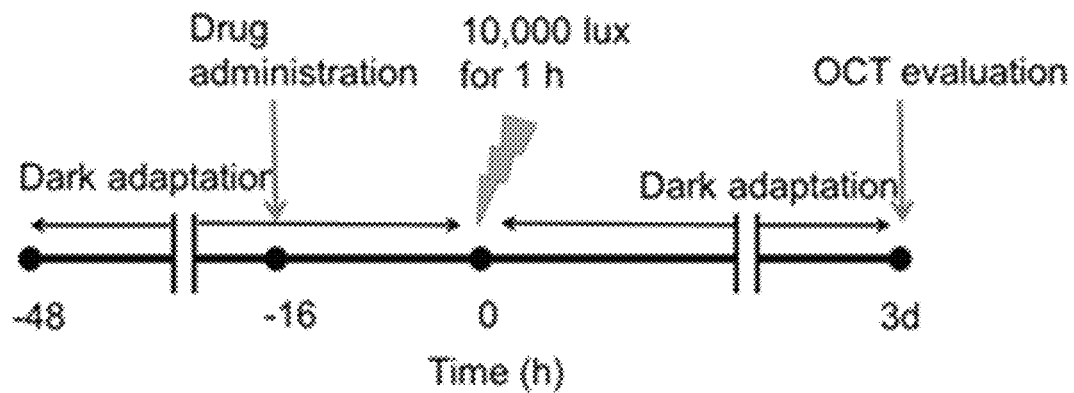
FIG. 1 illustrates a schematic representation of an experimental design of administering a retinylamine derivative described herein.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The terms "therapeutic agent," "drug" and "active agent" are used interchangeably herein to refer to a chemical material or compound which, when administered to an organism (human or animal, generally human) induces a desired pharmacologic effect.

By the terms "effective amount" or "pharmaceutically effective amount" of an agent as provided herein are meant a non-toxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. An appropriate "effective" amount in any individual case may be determined by one of ordinary skill in the art by reference to the pertinent texts and literature and/or using routine experimentation.

By "pharmaceutically acceptable" is meant a carrier comprised of a material that is not biologically or otherwise undesirable.

The term "transmembrane" refers to the passage of a substance into or through a body membrane, e.g., a mucosal membrane such as the gastrointestinal, sublingual, buccal, nasal, pulmonary, vaginal, corneal, or ocular membranes, so as to achieve a desired therapeutic or prophylactic effect.

The terms "absorption" and "transmembrane absorption" as used herein refer to the rate and extent to which a substance passes through a body membrane.

The term "controlled release" is intended to refer to any therapeutic agent-containing formulation in which the manner and profile of drug release from the formulation are controlled. The term "controlled release" refers to immediate as well as nonimmediate release formulations, with nonimmediate release formulations including but not limited to sustained release and delayed release formulations.

The term "delayed release" is used in its conventional sense to refer to a delay in release of a composition from a dosage form following oral administration, such that the majority of the composition is released in the lower gastrointestinal (GI) tract. After the dosage form reaches the intended release site, there may or may not be a further mechanism controlling the release of the composition from the dosage form. "Delayed release" may thus be an immediate release of all the contents of a drug dosage form, or it may involve controlled release in a sustained manner or in a staged or pulsatile fashion (e.g., when a multi-component device is utilized), wherein the term "sustained" means that release occurs during an extended time period, and the terms "staged" and "pulsatile" mean that release occurs in two or more spaced apart pulses.

The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds described herein can be delivered in prodrug form. Prodrugs can be prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intraocular, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt.

The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The phrase "therapeutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "RAL" means retinaldehyde. "Free RAL" is defined as RAL that is not bound to a visual cycle protein. The terms "trans-RAL" and "all-trans-RAL" are used interchangeably and mean all-trans-retinaldehyde.

The term "active ingredient," unless specifically indicated, is to be understood as referring to the retinylamine derivatives described herein.

The term "bioavailability" generally means the rate and/or extent to which the active ingredient is absorbed from a drug product and becomes systemically available and hence available at the site of action. See Code of Federal Regulations, Title 21, Part 320.1 (2003 ed.). For oral dosage forms, bioavailability relates to the processes by which the active ingredient is released from the oral dosage form and becomes systemically available and hence available at the site of action. Bioavailability data for a particular formulation provides an estimate of the fraction of the administered dose that is absorbed into the systemic circulation. Thus, the term "oral bioavailability" or "enteral bioavailability" refers to the fraction of a dose of a drug given orally or enterally that reaches the systemic circulation after a single administration to a subject.

The term "increase in oral bioavailability" or "increase in enteral bioavailability" refers to the increase in the bioavailability of a retinylamine derivative described herein when orally or enterally administered as compared to the bioavailability when retinylamine is orally or enterally administered without chemical modification alone. The increase in oral bioavailability can be from 5% to 20,000%, preferably from 200% to 20,000%, more preferably from 500% to 20,000%, and most preferably from 1000% to 20,000%.

Embodiments described herein relate to pharmaceutical compositions that include retinylamine derivatives and to their use in treating ocular disorders in subjects in need thereof. Modulation of retinoid cycle has been considered as an effective approach for preventive treatment of retinal degeneration. Retinylamine and its analogue emixustat (formerly ACU4429) have been identified as potent modulators of the retinoid cycle chemistry. Both compounds act as potent inhibitors of RPE65 and are effective to prevent retinal degeneration in experimental animals and human patients. A potential side effect of RPE65 inhibition is the blockage of retinoid cycle chemistry and, consequently, the loss of night vision or other side effects.

Sequestration of atRAL, a toxic byproduct in the retinoid cycle, by forming Schiff base with primary amines, including retinylamine, is a potential mechanism for effective protection against retinal degeneration in animal models of AMD and Stargardt disease. This mechanism of action can minimize the side effects of RPE65 inhibition.

It was found that retinylamine can be chemically modified with amino acids and peptides to provide retinylamine derivatives having improved stability, bioavailability, therapeutic efficacy, and safety profile compared to retinylamine. In some embodiments, the retinylamine derivatives formed by chemical modification with amino acids and peptides to improve their stability and ocular bioavailability and minimize their side effects can have the following formula:

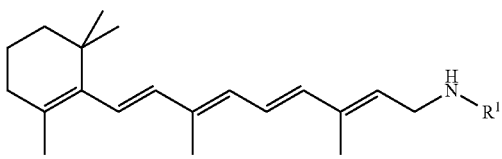

where $R^1$ is an amino acid residue, a dipeptide or a tripeptide that is linked to the retinylamine by an amide bond.

In some embodiments, $R^1$ can include at least one of L-phenylalanine, L-leucine, L-isoleucine, L-alanine, L-proline, L-valine, glycine, β-alanine, D-alanine, or D-valine. For example, $R^1$ can be selected from the group consisting of L-phenylalanine, L-leucine, L-isoleucine, L-alanine, L-proline, L-valine, glycine, β-alanine, D-alanine, D-valine, glycine-glycine, L-valine-glycine, and glycine-L-valine.

In other embodiments, $R^1$ can include at least one of L-valine or glycine. Examples of retinylamine derivatives in which $R^1$ can include at least one of L-valine or glycine are glycine, L-valine-glycine, and glycine-L-valine.

The chemical stability of the amino acid and peptide retinylamine derivatives is significantly improved over retinylamine Ret-$NH_2$ is readily protonated in aqueous solution under neutral or acidic condition to form ammonium, which can destabilize the conjugate polyene. The formation of amide bond at the primary amine after chemical modification prevents the protonation near the polyene, which improves the chemical stability. The derivatives can be readily absorbed by the body after oral administration. The amino acid and peptide derivatives can also have primary amines and readily form Schiff bases to sequester atRAL. The chemical modification can also introduce steric effect for binding of the derivatives with RPE65, which can block the inhibitive effect of retinylamine and alleviate potential side effects, Advantageously, the retinylamine derivatives demonstrate structure-dependent activities on preventing light-induced retinal degeneration in Abca4$^{-/-}$Rdh8$^{-/-}$ mice. The protecting effect is correlated with the biodistribution of the derivatives in the eye. The presence of the therapeutics in the eye at the time of exposure prevents retinal degeneration by sequestering atRAL via the formation of Schiff base.

Oral treatment of dark-adapted C57BL/6J mice with retinylamine derivatives described herein resulted in regeneration of 11-cis-retinal as compared to the mice untreated control after a strong light exposure. The slow regeneration with the retinylamine derivatives described herein can be attributed to the sequestration of atRAL by forming Schiff base. The low concentration of atRAL after Schiff base formation and slow hydrolysis of Schiff base back to atRAL can result in slow regeneration of 11-cis-retinal. Nevertheless, the regeneration was more rapid than that with Ret-$NH_2$. Rapid regeneration of 11-cis-retinal allows rapid recovery of normal retinoid cycle chemistry and retina function, and minimize potential side effect, including night blindness, after the treatment. As shown in the Examples, amino acid or peptide derivatives of Ret-$NH_2$ are effective to modulate retinoid cycle chemistry for preventing retinal degeneration with minimal side effects.

In some embodiments, the retinylamine derivatives can be provided in pharmaceutical compositions that are in used in methods of treating an ocular disorder or ophthalmic disease in a subject in need thereof. The methods can include administering to the subject a therapeutically effective amount of a pharmaceutical composition including the retinylamine derivative.

In some embodiments, a pharmaceutical composition that includes the retinylamine derivative described herein can be administered to a subject for treating, curing, preventing, ameliorating the symptoms of, or slowing, inhibiting, or stopping the progression of ocular or ophthalmic diseases or disorders. Representative ophthalmic diseases and disorders include, but are not limited to, macular degeneration, glaucoma, diabetic retinopathy, retinal detachment, retinal blood vessel occlusion, retinitis pigmentosa, autosomal dominant retinitis pigmentosa (ADRP), optic neuropathy, inflammatory retinal disease, diabetic maculopathy, hemorrhagic retinopathy, retinopathy of prematurity, optic neuropathy, proliferative vitreoretinopathy, retinal dystrophy, ischemia-reperfusion related retinal injury, hereditary optic neuropathy, metabolic optic neuropathy, Leber congenital amaurosis (LCA) including LCA arising from mutations in the LRAT and RPE65 genes, Stargardt's macular dystrophy, Sorsby's fundus dystrophy, Fundus albipunctatus, congenital stationary nightblindness (CSNB), Best disease, uveitis, age-related retinal dysfunction, a retinal injury, a retinal disorder associated with Parkinson's disease, a retinal disorder associated with viral infection, a retinal disorder related to light overexposure, and a retinal disorder associated with AIDS, a retinal disorder associated with Alzheimer's disease, and a retinal disorder associated with multiple sclerosis.

Vitamin A, retinol, plays essential roles in many biological processes including vision, immunity, growth, development, and cellular differentiation. Therefore, in some embodiments, a pharmaceutical composition that includes the retinylamine derivative described herein can be administered to a subject for retinoid replacement, supplementing the levels of endogenous retinoid. For example, a polysaccharide retinoid conjugate of the present invention can be administered to a subject having a vitamin A deficiency (VAD). In some embodiments a pharmaceutical composition that includes the retinylamine derivative described herein can be administered to a subject for the pharmacological inhibition of the retinoid cycle.

In some embodiments, methods of using a pharmaceutical composition that includes the retinylamine derivative described herein are provided to restore or stabilize photoreceptor function, or to ameliorate photoreceptor loss, in a vertebrate visual system.

The pharmaceutical composition that includes the retinylamine derivative described herein can be administered prophylactically or therapeutically to a vertebrate.

In some embodiments, the vertebrate eye is characterized as having age-related macular degeneration ("AMD"). AMD can be wet or dry forms. In AMD, vision loss occurs when complications late in the disease either cause new blood vessels to grow under the retina or the retina atrophies. Without intending to be bound by any particular theory, excessive production of waste products from the photoreceptors may overload the RPE. This is due to a shortfall of 11-cis-retinal available to bind opsin. Free opsin is not a stable compound and can spontaneously cause firing of the biochemical reactions of the visual cascade without the addition of light.

In other embodiments, the pharmaceutical composition that includes the retinylamine derivative described herein is administered to an aging subject, such as a human. As used herein, an aging human subject is typically at least 45, or at least 50, or at least 60, or at least 65 years old. The subject has an aging eye, which is characterized as having a decrease in night vision and/or contrast sensitivity.

The subject can include vertebrates, such as, human and non-human vertebrates. Examples of non-human vertebrates include mammals, such as dogs (canine), cats (feline), horses (equine) and other domesticated animals.

The pharmaceutical composition that includes the retinylamine derivative described herein can be substantially pure, in that it contains less than about 5% or less than about 1%, or less than about 0.1%, of other retinoids.

Pharmaceutical compositions that include the retinylamine derivatives described herein can be formulated for administration using pharmaceutically acceptable vehicles as well as techniques routinely used in the art. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may also be used.

The pharmaceutical compositions may be milled using known milling procedures, such as wet milling to obtain a particle size appropriate for tablet formation and for other formulation types. Finely divided (nanoparticulate) preparations of the compounds may be prepared by processes known in the art, for example see International Patent Application No. WO 02/00196 (SmithKline Beecham).

The pharmaceutical compositions including the retinylamine derivatives are intended to be administered orally or enterally (e.g., as a tablet, sachet, capsule, pastille, pill, boluse, powder, paste, granules, bullets or premix preparation, ovule, elixir, solution, suspension, dispersion, gel, syrup or as an ingestible solution). In addition, the pharmaceutical compositions described herein may be present as a dry powder for constitution with water or other suitable vehicle before use, optionally with flavoring and coloring agents. Solid and liquid compositions may be prepared according to methods well-known in the art. Such compositions may also contain one or more pharmaceutically acceptable carriers and excipients which may be in solid or liquid form.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

The tablets may contain excipients, such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents, such as magnesium stearate, stearic acid, glyceryl behenate and talc may be included.

Examples of pharmaceutically acceptable disintegrants for oral compositions include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of pharmaceutically acceptable dyes for the oral compositions include, but are not limited to, synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include, but are not limited to, hydroxypropylmethylcellulose, hydroxypropylcellulose and acrylate-methacrylate copolymers.

Examples of pharmaceutically acceptable sweeteners for the oral compositions include, but are not limited to, aspartame, saccharin, saccharin sodium, sodium cyclamate, xylitol, mannitol, sorbitol, lactose and sucrose.

Examples of pharmaceutically acceptable buffers include, but are not limited to, citric acid, sodium citrate, sodium bicarbonate, dibasic sodium phosphate, magnesium oxide, calcium carbonate and magnesium hydroxide.

Examples of pharmaceutically acceptable surfactants include, but are not limited to, sodium lauryl sulfate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Examples of pharmaceutically acceptable stabilizers and antioxidants include, but are not limited to, ethylenediaminetetra-acetic acid (EDTA), thiourea, tocopherol and butyl hydroxyanisole.

Pharmaceutical "slow release" capsules or "sustained release" compositions or preparations may be used and are generally applicable. Slow release formulations are generally designed to give a constant drug level over an extended period and may be used to deliver retinylamine derivatives described herein.

Examples of sustained-release preparations include semipermeable matrices of solid hydrophobic polymers containing the retinylamine derivative, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot (injectable microspheres composed of lactic acid-glycolic acid copolymer and leuprolide acetate); and poly-D-(−)-3-hydroxybutyric acid.

While polymers, such as ethylene-vinyl acetate and lactic acid-glycolic acid enable release of molecules for over 100 days, certain hydrogels can be uses for shorter time periods. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the retinyl amine derivatives. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 μm, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

The pharmaceutical compositions described herein may contain from 0.01 to 99% weight per volume of the retinylamine derivatives described herein.

The doses of the pharmaceutical compositions can be selected depending on the clinical status, condition and age of the subject, dosage form and the like.

For example, oral doses can typically range from about 0.01 to about 1000 mg, one to four times, or more, per day, week, or month. An exemplary dosing range for oral administration is from about 10 to about 250 mg one to three times per week.

Other embodiments described herein relate to retinylamine or retinylamine derivative therapeutic conjugate compositions that provide controlled release, delayed release, and/or sustained delivery of a therapeutic agent upon enteral administration of the composition to a subject. The release and/or delivery of the therapeutic agent is controlled, delayed, and/or sustained in nature, such that the release and/or delivery of the therapeutic agent from the dosage form is controlled, delayed, and/or sustained after oral administration, and, for example, such that it occurs in the lower gastrointestinal (GI) tract. That is, controlled, delayed, and/or sustained delivery or release of the therapeutic from the composition or dosage form may occur in a sustained fashion over an extended period of time (e.g., hours, days, or weeks), or in a staged or pulsatile fashion.

Oral administration is the most practical approach for drug delivery because of superior patient compliance. However, this route may not adequately control drug bioavailability and pharmacokinetics with conventional dosage forms, especially those that display rapid pharmacokinetics. A biocompatible polymer conjugate of Ret-$NH_2$ or Ret-$NH_2$ derivatives with a peptide spacer is effective for sustained release and prolonged therapeutic efficacy of Ret-$NH_2$. Conjugation of an acid sensitive Ret-$NH_2$ to a polymer via an amide bond can improve its stability in the acidic environment of the stomach. Ret-$NH_2$ then could be gradually released in the small intestine and colon to maintain a relatively stable effective drug concentration in the circulation over an extended period. Sustained drug release from the conjugate can reduce the overall dose and dosing frequency required to produce prolonged protection against light induced retinal degeneration. Reduced dose and dosing frequency can also minimize any dose-related toxic side effects.

In some embodiments, the therapeutic conjugate compositions include a biocompatible polymer and at least one retinylamine or retinylamine derivative linked to the biocompatible polymer with an oligopeptide spacer. The oligopeptide spacer is degradable by intestinal enzymes during digestion of the composition to provide controlled, delayed, and/or sustained delivery of the at least one retinylamine or retinylamine derivative upon enteral administration of the composition to a subject. The therapeutic conjugate compositions described herein have increased thermodynamic stability and absorption time of the retinylamine or retinylamine derivative upon enteral administration compared to administration of the retinylamine or retinylamine derivative alone. The therapeutic conjugate compositions can thus be used as highly dense therapeutic agents for the treatment of diseases or disorders where controlled release, delayed release, and/or sustained delivery of a therapeutic agent is desired. The controlled, delayed, and/or sustained release can allow therapeutic levels of retinylamine or retinylamine derivative to be maintained in the subject for house, days, and/or weeks without the need for constant and/or continuous administration of the retinoid.

In some embodiments, the oligopeptide linkage is a glycine-phenylalanine-leucine linkage that is cleavable or degradable under by intestinal enzymes of the lower gastrointestinal (GI) tract, e.g., intestines, to provide controlled, delayed, and/or sustained delivery or release of the retinylamine or retinylamine derivative to treat an ocular disorder, such as a retinal disease associated with inadequate production of 11-cis-retinal.

The biocompatible polymer can include any biocompatible to which the retinylamine or retinylamine derivative can be conjugated to using the spacer and which is suitable for enteral administration to a subject. Examples of biocompatible polymers include natural polymers, such as collagen, fibrin, gelatin, glycosaminoglycans (GAG), poly (hyaluronic acid), poly(sodium alginate), alginate, hyaluronan, and agarose. Other examples of biocompatible, polymers are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, polyethylene glycol, copolymers of polyethylene glycol and poly (lactide)s or poly(lactide-co-glycolide)s, biodegradable polyurethanes, and blends and/or copolymers thereof.

Still other examples of biocompatible polymers include chitosan, poly(ethylene oxide), poly (lactic acid), poly (acrylic acid), poly(vinyl alcohol), poly(urethane), poly(N-isopropyl acrylamide), poly(vinyl pyrrolidone) (PVP), poly (methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly (amide), poly(hydroxylacid), poly(sulfone), poly(amine), poly(saccharide), poly(HEMA), poly(anhydride), polyhydroxybutyrate (PHB), copolymers thereof, and blends thereof.

In some embodiments, embodiments the biocompatible polymer can be polyethylene glycol with an average molecular weight of at least 4 kDa, for example, about 20 kDa.

The therapeutic conjugate compositions described herein can be administered as prodrugs to give a sustained release of the active retinoid over time. Advantages thereof include a decrease in toxicity effects of the free retinoid, economizing of the amount of retinoid needed due to an increase in circulation time and facilitating solubilization of hydrophobic retinoids.

Thus, in another embodiment of the application, a method for treating an ocular disorder or ophthalmic disease in a subject includes administering to the subject a therapeutically effective amount of a composition described herein.

In some embodiments, a therapeutic conjugate composition described herein can be administered to a subject for treating, curing, preventing, ameliorating the symptoms of, or slowing, inhibiting, or stopping the progression of ocular or ophthalmic diseases or disorders. Representative ophthalmic diseases and disorders include, but are not limited to, macular degeneration, glaucoma, diabetic retinopathy, retinal detachment, retinal blood vessel occlusion, retinitis pigmentosa, autosomal dominant retinitis pigmentosa (ADRP), optic neuropathy, inflammatory retinal disease, diabetic maculopathy, hemorrhagic retinopathy, retinopathy of prematurity, optic neuropathy, proliferative vitreoretinopathy, retinal dystrophy, ischemia-reperfusion related retinal injury, hereditary optic neuropathy, metabolic optic neuropathy, Leber congenital amaurosis (LCA) including LCA arising from mutations in the LRAT and RPE65 genes, Stargardt's macular dystrophy, Sorsby's fundus dystrophy, Fundus albipunctatus, congenital stationary nightblindness (CSNB), Best disease, uveitis, age-related retinal dysfunction, a retinal injury, a retinal disorder associated with Parkinson's disease, a retinal disorder associated with viral infection, a retinal disorder related to light overexposure, and a retinal disorder associated with AIDS, a retinal disorder associated with Alzheimer's disease, and a retinal disorder associated with multiple sclerosis.

Administration of the therapeutic conjugate compositions to the vertebrate eye can reduce the deficiency of 11-cis-retinal and quench spontaneous misfiring of the opsin.

Administration of the therapeutic conjugate compositions can lessen the production of waste products and/or lessen drusen formation, and reduce or slow vision loss (e.g., choroidal neovascularization and/or chorioretinal atrophy).

In other embodiments, the therapeutic conjugate composition is administered to an aging subject, such as a human. As used herein, an aging human subject is typically at least 45, or at least 50, or at least 60, or at least 65 years old. The subject has an aging eye, which is characterized as having a decrease in night vision and/or contrast sensitivity.

The subject can include vertebrates, such as, human and non-human vertebrates. Examples of non-human vertebrates include mammals, such as dogs (canine), cats (feline), horses (equine) and other domesticated animals.

The therapeutic conjugate compositions can be substantially pure, in that it contains less than about 5% or less than about 1%, or less than about 0.1%, of other retinoids.

Therapeutic conjugate compositions described herein can be formulated for administration using pharmaceutically acceptable vehicles as well as techniques routinely used in the art. A vehicle can be selected according to the solubility of the polysaccharide retinoid conjugate. Examples of pharmaceutical compositions include those that are administrable enterally or orally.

Examples of oral dosage forms include tablets, pills, sachets, or capsules of hard or soft gelatin, methylcellulose or of another material easily dissolved in the digestive tract. Examples of nontoxic solid carriers can include pharmaceutical grades of mannitol, lactose, starch, magnesium stearate, sodium saccharin, talcum, cellulose, glucose, sucrose, magnesium carbonate, and the like. (See, e.g., Remington "Pharmaceutical Sciences", 17 Ed., Gennaro (ed.), Mack Publishing Co., Easton, Pa. (1985).)

The doses of the therapeutic conjugate compositions can be selected depending on the clinical status, condition and age of the subject, dosage form and the like.

For example, oral doses can typically range from about 0.01 to about 1000 mg, one to four times, or more, per day, week, or month. An exemplary dosing range for oral administration is from about 10 to about 250 mg one to three times per week.

Example 1

In this Example, we modified the structure of retinylamine (Ret-$NH_2$) to improve its pharmaceutical and pharmacological properties and to minimize its potential side effects. Structural modification of retinylamine with amino acids and peptides that bind to the amino acid and peptide transporters can enhance the gastrointestinal absorption of retinylamine in the eye and its uptake by the eye. The formation of the amide bond of the primary amine of the drug can improve its stability, especially in the acidic environment after oral administration. Most importantly, the structural modification can alleviate the inhibition of RPE65 isomerase in the visual cycle by blocking binding to the isomerase due to the structural alteration from the amino acids or peptides, which can minimize side effects associated with its inhibition.

We designed and synthesized a library of thirteen amino acid and peptide derivatives of retinylamine. The efficacy of the derivatives for preventing light-induced retinal degeneration was assessed in Abca4$^{-/-}$Rdh8$^{-/-}$ mice. The cell transport, uptake, and pharmacokinetics of the lead derivatives were evaluated in vitro and in vivo in wild-type mice. Sequestration of atRAL via forming Schiff base and the effect on RPE65 and visual cycle of the leads were assessed in vitro and in vivo. The potential side effects on vision of the lead drug were also assessed in wild-type mice.

Methods

Animals and Treatments

Abca4$^{-/-}$Rdh8$^{-/-}$ double knockout mice were housed in the animal facility at the School of Medicine, Case Western Reserve University, where they were maintained under either complete darkness or a 12-h light (~10 lx) and 12-h dark cycle. All retinylamine tested were dissolved or suspended in 100 μl of vegetable oil with less than 10% (v/v) DMSO and were administered by oral gavage with a 22-gauge feeding needle. Experimental manipulations in the dark were done under dim red light transmitted through a Kodak No. 1 safelight filter (transmittance >560 nm). All animal procedures and experiments were approved by the Case Western Reserve University Animal Care Committees and conformed to recommendations of the American Veterinary Medical Association Panel on Euthanasia and the Association of Research for Vision and Ophthalmology.

Induction of Light-Induced Retinal Degeneration in Abca4$^{-/-}$Rdh8$^{-/-}$ Mice After dark adaptation for 48 h, one or two Abca4$^{-/-}$Rdh8$^{-/-}$ mice with pupils dilated by 1% tropicamide were exposed to fluorescent light (10,000 lx; 150-W spiral lamp, Commercial Electric) for 60 min in a white plastic bucket (Papersmith) with food and water and then kept in the dark. Histological and biochemical experiments were performed 3 days after exposure.

Ultra-High Resolution Spectral-Domain OCT and Scanning Laser Ophthalmoscopy Imaging Ultra-high resolution spectral-domain OCT (SD-OCT; Bioptigen) and Heidelberg Retinal Angiograph II SLO (Heidelberg Engineering) were used for in vivo imaging of mouse retinas. Mice were anesthetized by intraperitoneal injection of a cocktail (20 μl g-1 body weight) containing ketamine (6 mg ml-1) and xylazine (0.44 mg ml-1) in 10 mM sodium phosphate, pH 7.2, and 100 mM NaCl. Pupils were dilated with 1% tropicamide. Four pictures acquired in the B-scan mode were used to construct each final averaged SD-OCT image.

ERGs

All ERG procedures were performed by published methods. For single-flash recording, the duration of white-light flash stimuli (from 20 μs to 1 ms) was adjusted to provide a range of illumination intensities (from −3.7 to 1.6 log cd s m-2). Three to five recordings were made at sufficient intervals between flash stimuli (from 3 s to 1 min) to allow recovery from any photobleaching effects.

Histology

Mouse eyes were fixed for 24 h by rocking in a fixation solution (2 ml/eye) containing 4% paraformaldehyde and 1% glutaraldehyde in PBS. The tissue was processed through a series of ethanols, xylenes, and paraffins in a Tissue-Tek VIP automatic processor (Sakura, Torrance, Calif., USA), and 5-μm sections were cut using a Microm HM355 paraffin microtome (Thermo Fisher Scientific, Waltham, Mass., USA) and stained with hematoxylin and eosin (H&E) stain. Images of stained sections were captured by a Leica CTR6000 microscope attached to a CCD camera (Micropublisher 5.0 RTV, Qimaging Surray BC, Canada).

Pharmacokinetic Distribution of N-Retinylamides and Retinylamine Derivatives in the Liver, Eye and Blood Female C57BL mice (4-week-old) were randomly divided into seven groups, six treated groups and one control group. Free Ret-$NH_2$ (3.5 mol per mouse, dissolved in DMSO and dispersed in vegetable oil) or retinylamine derivatives (Ret-Gly, Ret-L-Val-Gly, Ret-L-Phe, Ret-L-Leu, Ret-L-Val, 3.5 mol per mouse, dissolved in DMSO and dispersed in vegetable oil) was administered by gastric gavage, control group was only gavaged vegetable oil. Then at each predetermined time point (2 and 16 h after drug administration), 3 mice were sacrificed. The liver and eye balls were collected to determine tissue N-retinylamide content for pharmacokinetic analysis. A portion of the liver tissue (0.3-0.5 g) was weighed, homogenized in 2 mL 1:1 ethanol:PBS solution and the eye balls were similarly processed (eye balls were combined for 3 mice). N-Retinylamides were extracted in 4 mL hexane, concentrated, and reconstituted to a 300 µL volume for liver (200 µL for eye). Normal-phase HPLC (Agilent-Zorbax SIL; 5 µm; 4.5×250 mm; flow rate of 1.4 mL/min; 80:20 hexane:ethyl acetate (v:v); detection at 325 nm) was utilized to determine N-retinylamide concentration in these tissues.

Female C57BL mice (4-week-old) were randomly divided into seven groups, six treated groups and one control group. Free Ret-$NH_2$ (3.5 mol per mouse, dissolved in DMSO and dispersed in vegetable oil) or retinylamine derivative (Ret-Gly, Ret-L-Val-Gly, Ret-L-Phe, Ret-L-Leu, Ret-L-Val, 3.5 mol per mouse, dissolved in DMSO and dispersed in vegetable oil) was administered by gastric gavage, control group was only gavaged vegetable oil. Then at each predetermined time point (2 and 16 h after drug administration), 3 mice were sacrificed. The liver and eye balls were collected to determine tissue drug content for pharmacokinetic analysis. A portion of the liver tissue (0.3-0.5 g) was weighed, homogenized in 2 mL 1:1 ethanol:PBS solution and the eye balls were similarly processed. Retinylamine or its derivative was extracted in 4 mL ethyl acetate, concentrated, and reconstituted to a 300 µL volume for liver (200 µL for eye). Reverse-phase HPLC (analytical C18 reverse column; 5 µm; 250 mm×4.6 mm; flow rate of 1.0 mL/min; 60:40 acetonitrile:$H_2O$ (v:v) with 0.05% trifluoroacetic acid; detection at 325 nm) was utilized to determine retinylamine or its derivative in these tissues.

Blood was collected into tube with EDTA centrifuge and take serum, homogenized in 2 mL 1:1 ethanol:PBS solution. Retinylamine or its derivative was extracted in 4 mL ethyl acetate, concentrated, and reconstituted to a 300 µL volume. Reverse-phase HPLC (analytical C18 reverse column; 5 µm; 250 mm×4.6 mm; flow rate of 1.0 mL/min; 60:40 acetonitrile:$H_2O$ (v:v) with 0.05% trifluoroacetic acid; detection at 325 nm) was utilized to determine retinylamine or its derivative in serum.

$Lrat^{-/-}$ mice were obtained and genotyped as described previously. Animals were gavaged with 1 mg of Ret-$NH_2$, Ret-L-Val (RV) and Ret-Gly-L-Val (RGV) dissolved in 100 µl of vegetable oil 16 h prior to analysis. The liver and eye balls were collected to determine tissue N-retinylamide content for pharmacokinetic analysis. A portion of the liver tissue (0.3-0.5 g) was weighed, homogenized in 2 mL 1:1 ethanol:PBS solution and the eye balls were similarly processed (eye balls were combined for 3 mice). N-Retinylamides were extracted in 4 mL hexane, concentrated, and reconstituted to a 300 µL volume for liver (200 µL for eye). Normal-phase HPLC (Agilent-Zorbax SIL; 5 µm; 4.5×250 mm; flow rate of 1.4 ml/min; 80:20 hexane:ethyl acetate (v:v); detection at 325 nm) was utilized to determine N-retinylamide concentration in these tissues.

In Vivo RPE65 Inhibition

The retinylamine derivatives (31 RVG and 3b RF) or Ret-NH2 were administered by oral gavage at same mole dose 1.75 µmol per mouse into dark-adapted C57BLwild-type female mice (n=3) at 16 h prior to photo-bleach. After photo-bleach (7000 lux, 10 min), mice were kept the dark room for 24 h to allow the visual cycle to recovery. Mice were then sacrificed and eyes were extracted for analysis. Mice without treatment prior to photo-bleach were set as control. Retinoid extraction was done by manually homogenizing eyes in 1 mL of 1:1 ethanol:PBS solution containing 40 mM hydroxylamine Retinoids were extracted in 4 mL hexane, concentrated, and reconstituted to a volume of 200 µL. Normal-phase HPLC (Agilent-Zorbax SIL; 5 µm; 4.5× 250 mm; flow rate of 1.4 mL/min; 90:10 hexane:ethyl acetate (v:v); detection at 325 nm) was utilized to analyze retinoid concentrations. In vivo RPE65 inhibition was analyzed by quantifying the amount of 11-cis-retinal within each eye.

RPE Microsomal Preparations

Bovine RPE microsomes, isolated from RPE homogenates by differential centrifugation as previously described, were resuspended in 10 mM Tris HCl, pH 7.2, 1 µM leupeptin and 1 mM DTT to achieve a total protein concentration of ~5 mg ml-1. To destroy endogenous retinoids, 200-µl aliquots of RPE microsomes placed in a quartz cuvette were irradiated for 5 min at 0° C. with a ChromatoUVE transilluminator (model TM-15; UVP).

Retinoid Cycle Enzyme Assays: Retinoid Isomerase Activity

All assays were performed under dim red light. 2 µl of the synthesized retinylamine derivatives (RF and RVG) (DMF, 0.5-10 mM) was added into 10 mM Bis-Tris propane buffer (pH 7.4) containing 150 µg RPE microsomes, 1% BSA, 1 mM disodium pyrophosphate and 20 µM apo Retinaldehyde-binding protein 1 (CRALBP). The resulting mixture was pre-incubated at room temperature for 5 min. Then 1 µl all-trans-retinol (DMF, 20 mM) was added. The resulting mixture was incubated at 37° C. for 1 h. Reaction was quenched by addition of 300 µl methanol, and the products were extracted with 300 µl hexanes. Production of 11-cis-retinol was quantified by normal phase HPLC with 10% (v/v) ethyl acetate in hexanes as eluent. Flow rate was 1.4 ml·$min^{-1}$. Retinoids were detected by monitoring absorbance at 325 nm and quantified base on a standard curve reflecting relation between amount of 11-cis-retinol and area under the corresponding chromatography peak.

In Vitro NIH3T3 Cell Assay

The cells were plated in 6-well plates using Dulbecco's Modified Eagle Medium (DMEM) and allowed to grow to 90% confluency. The cells were then incubated with DMEM containing 10 µM all-trans-retinol and 4.5 µM retinylamine, or derivatives for 16 hours under dark room conditions. Control groups included a positive control (all-trans-retinol only) and a negative control (no treatment). Cells and medium were collected after 16 hours of incubation. Samples were treated with 2 ml of methanol, homogenized, and saponified with 1 M KOH at 37° C. for 2 hours prior to extraction with hexane. The resulting hexane phase was collected, dried using a SpeedVac, and redissolved in 250 µl of hexane, and retinoid composition was determined by normal phase HPLC.

All-Trap-Retinal Shiff Base Formation

Incubate Ret-$NH_2$ and retinylamine derivatives RVG, RF (0.2 mM) with all-trans-retinal (2 mM) in ethanol 2 h at room temperature, retinyl imines separated by reverse phase HPLC were identified on the basis of both their characteristic UV-vis spectra upon protonation and spectra obtained by mass spectrometry (MS). HPLC condition: analytical C18 reverse column; 5 µm; 250 mm×4.6 mm; flow rate of 0.5 mL/min; mobile phase acetonitrile:$H_2O$ (v:v) with 0.05% trifluoroacetic acid (0-15 min acetonitrile from 50% to 100%, 15-30 min 100% acetonitrile); detection at 325 nm.

Caco-2 Cell Assay

1. Coating and preparing culture inserts for seeding: Rat tail collagen was diluted 1:9 with 0.5% acetic acid. The resulting solution (200 ul) was added to each insert to coat the surface. The inserts were air-dried overnight, followed by a UV irradiation for 45 min to sterilize the inserts. 2. Seeding cells onto an insert: A concentration of $4\times10^5$ cells/well EMEM solution containing 20% FBS was added to the precoated insert. Another 2 ml of fresh EMEM media was added to the other side (bottom). The media was changed after 1 day of incubation and every other day after that. The cells were cultured for 21 days until they were mature. 3. Transport experiment: The media was aspirated out. The cell monolayers were washed with PBS three times. Cells were further incubated with PBS for 1 h under 37° C. to allow them to release all the materials that may be taken up during incubation. PBS solution was removed and the prodrug solution (500 μM in 2.0 ml PBS (pH=6) solution) was loaded to the apical side. The basolateral side was loaded with 2.5 ml fresh PBS solution. The plates were incubated under 37° C. Samples of 200 μl were withdrawn from the basolateral side at several time points within 24 h. The drug release amount was determined by UV spectrometer.

The ARPE19 cells (human RPE cells purchased from American Type Culture Collection) were plated in 6-well plates using Dulbecco's Modified Eagle Medium (DMEM) and allowed to grow to 90% confluency. The cells were then incubated with DMEM containing 10 μM derivatives for 16 hours under dark room conditions. Control group was cell without drug. Medium was removed and cells were washed three times by PBS after 16 h of incubation. Cells were then collected. Samples were treated with 400 μl of methanol, homogenized at 37° C. for 1 h, followed by a centrifugation. The 100 μl of the supernatant was analyzed by reverse phase HPLC. Reverse-phase HPLC (analytical C18 reverse column; 5 μm; 250 mm×4.6 mm; flow rate of 1.0 mL/min; 60:40 acetonitrile:$H_2O$ (v:v) with 0.05% trifluoroacetic acid; detection at 325 nm) was utilized to determine retinylamine or its derivative in serum.

Synthesize Retinylamine Derivatives

All commercially available reagents and solvent were used as analytically pure substances as received. Reactions were monitored by thin-layer chromatography (TLC) on silica gel plates (60 $F_{254}$) with a fluorescent indicator, and independently visualized with UV light. Intermediates and target molecules retinylamine derivatives were purified by column chromatography on silica (Silica gel grade: 200-400 mesh, 40-63 μm). All new compounds gave satisfactory spectroscopic analyses $^1$H NMR, $^{13}$C NMR). NMR spectra were recorded at 400 MHz in $CDCl_3$ or Acetone-$d_6$ and chemical shift values (δ) are given in ppm. $^1$H NMR spectra are reported in parts per million (δ) relative to the residual (indicated) solvent peak. Data for $^1$H NMR are reported as follows: chemical shift (δ ppm), multiplicity (s=singlet, bs=broad singlet, d=doublet, t=triplet, q=quartet, dd=double double, ddd=double double doublet, m=multiplet, cm=complex multiplet), integration, and coupling constants in Hz. $^{13}$C NMR spectra were obtained on 400 MHz spectrometers (100 MHz actual frequency) and are reported in parts per million (δ) relative to the residual (indicated) solvent peak. Matrix-assisted laser desorption/ionization time-of-flight (MALDI-TOF) mass spectra were acquired on a Bruker Autoflex III MALDI-TOF MS in a linear mode with 2,5-dihydroxybenzoic acid (2,5-DHB) as a matrix. Ion-pairing reverse-phase HPLC (RP-HPLC) was performed on an Agilent 1100 series HPLC system fitted with a Beckman Coulter Ultrasphere ODS 4.6 mm×25 cm, 5 μm pore size column. HPLC conditions: mobile phase of $H_2O$:Acetonitrile (40:60, v/v) with 0.05% trifluoroacetic acid, flow rate of 1.0 mL/min and UV detector set at 325 nm.

General Procedure for Synthesis of Retinylamine Derivatives

Retinylamine (Ret-$NH_2$) was synthesized and purified according to the reference published by Golczak et al (*Proc Natl Acad Sci USA*, 2005, 102, 8162-8167).

(2E,4E,6E,8E)-3,7-dimethyl-9-(2,6,6-trimethylcyclohex-1-en-1-yl)nona-2,4,6,8-tetraen-1-amine (2, Ret-$NH_2$): yield 23.5%; $^1$H NMR (400 MHz, $CDCl_3$) δ 6.56 (dd, J=15.2, 11.3 Hz, 1H), 6.27 (d, J=15.1 Hz, 1H), 6.21-6.04 (m, 3H), 5.58 (t, J=6.9 Hz, 1H), 3.47 (t, J=2.8 Hz, 2H), 2.92 (s, 2H), 2.01 (t, J=6.3 Hz, 2H), 1.94 (d, J=4.5 Hz, 3H), 1.84 (d, J=7.1 Hz, 3H), 1.70 (t, J=3.4 Hz, 3H), 1.65-1.56 (m, 2H), 1.49-1.41 (m, 2H), 1.02 (s, 6H). MALDI-TOF m/z [M-$NH_3$]$^+$ calcd. for $C_{20}H_{18}$: 268.219, found: 268.857.

100 mL flask was charged under atmosphere of nitrogen with Fmoc-$R^1$ (2.0 mmol, 1.0 equiv.), 1-Ethyl-3-(3-dimethylaminopropyl)carbodiimide (EDC) (383 mg, 2.0 mmol, 1.0 equiv.), Hydroxybenzotriazole (HOBt) (270 mg, 2.0 mmol, 1.0 equiv.), N, N-diisopropylethylamine (517 mg, 4.0 mmol, 2.0 equiv.), retinylamine (571 mg, 2.0 mmol, 1.0 equiv.) dissolved in dry DMF (20 mL) at room temperature. Stirring was continued at room temperature for 2-3 h and quenched with water. The intermediate Fmoc protected retinylamine derivative (Ret-$R^1$-Fmoc) was extracted by ethyl acetate and washed with brine and dried over $Na_2SO_4$. The crude product was purified by silica gel column chromatography with hexane and ethyl acetate. 10 mL 20% piperidine in dimethylformamide was added to Ret-$R^1$-Fomc to remove Fmoc. The crude product was purified by silica gel column chromatography with ethyl acetate and MeOH with 5% $NH_3$.

(S)-2-amino-N-((2E,4E,6E,8E)-3,7-dimethyl-9-(2,6,6-trimethylcyclohex-1-en-1-yl)nona-2,4,6,8-tetraen-1-yl)propanamide (3a, Ret-L-Ala): yield 17.5% (125 mg); $^1$H NMR (400 MHz, Acetone-$d_6$) δ 6.63 (dd, J=15.1, 11.3 Hz, 1H), 6.29 (d, J=15.2 Hz, 1H), 6.20-6.05 (m, 3H), 5.51 (t, J=6.8 Hz, 1H), 3.97 (d, J=7.0 Hz, 2H), 3.88 (q, J=7.0 Hz, 1H), 2.00 (t, J=6.2 Hz, 2H), 1.94 (s, 3H), 1.85 (s, 3H), 1.69 (s, 3H), 1.64-1.56 (m, 2H), 1.49-1.41 (m, 2H), 1.17 (d, J=7.0 Hz, 3H), 1.00 (s, 6H). $^{13}$C NMR (100 MHz, Acetone-$d_6$) δ 173.4, 138.2, 138.0, 137.1, 136.3, 135.5, 130.9, 129.4, 128.9, 126.3, 124.6, 59.2, 39.7, 36.8, 34.2, 33.0, 28.7, 21.4, 19.3, 19.0, 12.2, 12.1. MALDI-TOF m/z, [M]$^{\cdot+}$ calcd for $C_{23}H_{36}N_2O$: 356.283, found: 355.788.

(S)-2-amino-N-((2E,4E,6E,8E)-3,7-dimethyl-9-(2,6,6-trimethylcyclohex-1-en-1-yl)nona-2,4,6,8-tetraen-1-yl)-4-methylpentanamide (3b, Ret-L-Leu): yield 26.8% (214 mg); $^1$H NMR (400 MHz, Acetone-$d_6$) δ 6.63 (dd, J=15.1, 11.3 Hz, 1H), 6.29 (d, J=15.2 Hz, 1H), 6.24-6.02 (m, 3H), 5.50 (t, J=6.9 Hz, 1H), 4.12-3.88 (m, 3H), 2.00 (m, 2H), 1.94 (s, 3H), 1.85 (s, 3H), 1.69 (s, 3H), 1.63-1.55 (m, 4H), 1.50-1.40 (m, 3H), 1.01 (s, 6H), 0.87 (dd, J=13.8, 6.3 Hz, 6H). $^{13}$C NMR (100 MHz, Acetone-$d_6$) δ 172.8, 138.2, 138.0, 137.1, 136.2, 135.4, 130.9, 129.4, 128.9, 126.3, 124.5, 63.0, 44.1, 39.7, 36.8, 34.2, 32.9, 28.7, 24.6, 22.9, 22.3, 21.4, 19.3, 12.2, 12.0. MALDI-TOF m/z, [M]$^{\cdot+}$, calcd. for $C_{26}H_{42}N_2O$: 398.330, found: 398.809.

(2S,3S)-2-amino-N-((2E,4E,6E,8E)-3,7-dimethyl-9-(2,6,6-trimethylcyclohex-1-en-1-yl)nona-2,4,6,8-tetraen-1-yl)-3-methylpentanamide (3c, Ret-L-Ile): yield 31.2% (249 mg); $^1$H NMR (400 MHz, Acetone-$d_6$) δ 6.63 (dd, J=14.9, 11.3 Hz, 1H), 6.29 (d, J=15.1 Hz, 1H), 6.12 (d, J=16.9, 10.0 Hz, 3H), 5.51 (t, J=6.6 Hz, 1H), 4.11-3.76 (m, 3H), 2.09-

2.01 (m, 2H), 1.95 (s, 3H), 1.86 (s, 3H), 1.69 (s, 3H), 1.63-1.56 (m, 2H), 1.49-1.40 (m, 2H), 1.22-1.14 (m, 2H), 0.99 (d, J=13.4 Hz, 6H), 0.85 (dd, J=11.9, 7.1 Hz, 6H). $^{13}$C NMR (100 MHz, Acetone-d$_6$) δ 171.7, 138.2, 138.0, 137.1, 136.2, 135.4, 130.9, 129.4, 128.9, 126.3, 124.5, 68.7, 40.3, 39.7, 36.7, 34.2, 32.9, 28.7, 25.3, 21.4, 19.3, 15.4, 12.2, 12.1, 11.7. MALDI-TOF m/z [M]$^{•+}$ calcd. for C$_{26}$H$_{42}$N$_2$O: 398.330, found: 398.838.

(S)-2-amino-N-((2E,4E,6E,8E)-3,7-dimethyl-9-(2,6,6-trimethylcyclohex-1-en-1-yl)nona-2,4,6,8-tetraen-1-yl)-3-methylbutanamide (3d, Ret-L-Val): yield 22.4% (172 mg); $^1$H NMR (400 MHz, CDCl$_3$) δ 7.32 (t, J=5.2 Hz, 1H), 6.50 (dd, J=15.1, 11.3 Hz, 1H), 6.18 (d, J=15.1 Hz, 1H), 6.08-5.91 (m, 3H), 5.41 (t, J=7.0 Hz, 1H), 3.94 (t, J=6.3 Hz, 2H), 3.16 (d, J=3.9 Hz, 1H), 2.19 (m, 2H), 1.94 (s, 3H), 1.87 (s, 3H), 1.79 (s, 3H), 1.63 (s, 3H), 1.53 (m, 2H), 1.43-1.32 (m, 2H), 0.94 (s, 6H), 0.91 (d, J=7.0 Hz, 3H), 0.75 (d, J=6.8 Hz, 3H). $^{13}$C NMR (100 MHz, CDCl$_3$) δ 174.3, 138.0, 137.8, 137.2, 136.4, 136.2, 130.3, 129.4, 127.5, 126.8, 124.9, 60.3, 39.8, 37.4, 34.4, 33.2, 31.1, 29.1, 21.9, 19.9, 19.4, 16.4, 12.9, 12.8. MALDI-TOF m/z [M]$^{•+}$ calcd. for C$_{25}$H$_{40}$N$_2$O: 384.314, found: 384.750.

(S)-2-amino-N-((2E,4E,6E,8E)-3,7-dimethyl-9-(2,6,6-trimethylcyclohex-1-en-1-yl)nona-2,4,6,8-tetraen-1-yl)-3-phenylpropanamide (3e, Ret-L-Phe): yield 38.5% (333 mg); $^1$H NMR (400 MHz, Acetone-d$_6$) δ 7.37-7.00 (m, 6H), 6.64 (dd, J=15.1, 11.3 Hz, 1H), 6.29 (d, J=15.1 Hz, 1H), 6.23-6.02 (m, 3H), 5.47 (t, J=6.8 Hz, 1H), 4.14-3.85 (m, 2H), 3.20 (dd, J=12.9, 3.4 Hz, 1H), 2.85-2.66 (m, 1H), 2.01 (dd, J=10.3, 4.0 Hz, 2H), 1.95 (s, 3H), 1.86 (s, 3H), 1.69 (s, 3H), 1.60 (ddd, J=8.8, 8.0, 4.5 Hz, 2H), 1.50-1.41 (m, 2H), 1.02 (s, 6H). $^{13}$C NMR (100 MHz, Acetone-d$_6$) δ 172.1, 138.8, 138.19, 138.0, 137.1, 136.3, 135.5, 131.0, 130.1, 129.3, 128.9, 128.2, 126.4, 126.3, 124.6, 65.9, 40.7, 39.7, 36.9, 34.7, 33.0, 28.8, 21.5, 19.4, 12.3, 12.2. MALDI-TOF m/z [M+Na]$^+$ calcd. for C$_{29}$H$_{40}$N$_2$ONa: 455.304, found: 454.833.

(R)-2-amino-N-((2E,4E,6E,8E)-3,7-dimethyl-9-(2,6,6-trimethylcyclohex-1-en-1-yl)nona-2,4,6,8-tetraen-1-yl)propanamide (3f, Ret-D-Ala): yield 7.9% (56 mg); $^1$H NMR (400 MHz, Acetone-d$_6$) δ 6.62 (dd, J=15.0, 11.2 Hz, 1H), 6.28 (d, J=15.2 Hz, 1H), 6.19-6.00 (m, 3H), 5.49 (t, J=6.9 Hz, 1H), 3.96 (t, J=5.6 Hz, 2H), 3.85 (q, J=6.9 Hz, 1H), 1.98 (t, J=6.3 Hz, 2H), 1.93 (d, J=1.0 Hz, 3H), 1.84 (d, J=1.0 Hz, 3H), 1.67 (d, J=0.8 Hz, 3H), 1.62-1.54 (m, 2H), 1.48-1.40 (m, 2H), 1.14 (d, J=7.0 Hz, 3H), 0.99 (s, 6H). $^{13}$C NMR (100 MHz, Acetone-d$_6$) δ 173.3, 138.2, 138.0, 137.1, 136.2, 135.4, 130.9, 129.4, 128.9, 126.3, 124.6, 59.2, 39.7, 36.7, 34.2, 32.9, 28.7, 21.3, 19.3, 18.9, 12.1, 12.0. MALDI-TOF m/z [M]$^{•+}$ calcd. for C$_{23}$H$_{36}$N$_2$O: 356.283, found: 356.694.

(R)-2-amino-N-((2E,4E,6E,8E)-3,7-dimethyl-9-(2,6,6-trimethylcyclohex-1-en-1-yl)nona-2,4,6,8-tetraen-1-yl)-3-methylbutanamide (3g, Ret-D-Val): yield 17.3% (133 mg); $^1$H NMR (400 MHz, Acetone-d$_6$) δ 6.61 (dd, J=15.1, 11.3 Hz, 1H), 6.27 (d, J=15.2 Hz, 1H), 6.17-6.02 (m, 3H), 5.49 (t, J=6.9 Hz, 1H), 4.07-3.84 (m, 2H), 3.72 (d, J=4.6 Hz, 1H), 3.45-3.08 (m, 2H), 1.98 (d, J=6.0 Hz, 2H), 1.92 (d, J=0.8 Hz, 3H), 1.84 (d, J=0.9 Hz, 3H), 1.66 (t, J=1.6 Hz, 3H), 1.61-1.55 (m, 2H), 1.48-1.40 (m, 2H), 0.99 (s, 6H), 0.83 (dd, J=14.7, 6.9 Hz, 6H). $^{13}$C NMR (100 MHz, Acetone-d$_6$) δ 171.81, 138.17, 137.98, 137.13, 136.11, 135.40, 130.90, 129.47, 128.84, 126.26, 124.51, 69.48, 39.66, 36.68, 34.21, 33.22, 32.85, 28.68, 21.35, 19.29, 18.98, 17.79, 12.16, 12.04. MALDI-TOF m/z [M+Na]$^+$ calcd. for C$_{25}$H$_{40}$N$_2$ONa: 407.304, found: 406.704.

3-amino-N-((2E,4E,6E,8E)-3,7-dimethyl-9-(2,6,6-trimethylcyclohex-1-en-1-yl)nona-2,4,6,8-tetraen-1-yl)propanamide (3h, Ret-β-Ala): yield 14.0% (100 mg); $^1$H NMR (400 MHz, Acetone-d$_6$) δ 6.62 (dd, J=15.1, 11.3 Hz, 1H), 6.28 (dd, J=15.2, 8.4 Hz, 1H), 6.21-6.01 (m, 3H), 5.62-5.43 (m, 1H), 3.90 (d, J=6.9 Hz, 2H), 3.39 (t, J=6.8 Hz, 2H), 2.38 (t, J=6.8 Hz, 2H), 1.98 (d, J=6.2 Hz, 2H), 1.92 (s, 3H), 1.83 (d, J=0.9 Hz, 3H), 1.67 (d, J=0.8 Hz, 3H), 1.57 (td, J=6.3, 2.6 Hz, 2H), 1.47-1.40 (m, 2H), 0.99 (s, 6H). $^{13}$C NMR (100 MHz, Acetone-d$_6$) δ 171.3, 138.1, 138.0, 137.1, 136.2, 135.4, 130.9, 129.4, 128.9, 126.3, 124.5, 47.5, 39.6, 37.3, 37.0, 34.2, 32.9, 28.6, 21.3, 19.3, 12.1, 12.0. MALDI-TOF m/z, [M]$^{•+}$ calcd. for C$_{23}$H$_{36}$N$_2$O: 356.283, found: 356.734.

(S)—N-((2E,4E,6E,8E)-3,7-dimethyl-9-(2,6,6-trimethyl-cyclohex-1-en-1-yl)nona-2,4,6,8-tetraen-1-yl)pyrrolidine-2-carboxamide (3i, Ret-L-Pro): yield 20.6% (158 mg); $^1$H NMR (400 MHz, Acetone-d$_6$) δ 6.63 (dd, J=15.1, 11.3 Hz, 1H), 6.29 (d, J=15.1 Hz, 1H), 6.20-6.04 (m, 3H), 5.51 (t, J=6.9 Hz, 1H), 3.93 (d, J=7.0 Hz, 2H), 3.65 (dd, J=8.8, 5.5 Hz, 1H), 2.88 (ddt, J=22.8, 10.3, 6.5 Hz, 2H), 2.00 (d, J=5.2 Hz, 2H), 1.94 (s, 3H), 1.86 (s, 3H), 1.69 (s, 3H), 1.66-1.57 (m, 6H), 1.48-1.43 (m, 2H), 1.01 (s, 6H). $^{13}$C NMR (100 MHz, Acetone-d$_6$) δ 174.8, 138.2, 138.0, 137.1, 136.3, 135.4, 130.9, 129.3, 128.9, 126.3, 124.6, 60.7, 47.1, 39.7, 36.9, 34.3, 33.0, 30.8, 28.8, 26.2, 21.5, 19.4, 12.3, 12.2. MALDI-TOF m/z [M]$^{•+}$ calcd. for C$_{25}$H$_{38}$N$_2$O: 382.298, found: 382.711.

2-amino-N-((2E,4E,6E,8E)-3,7-dimethyl-9-(2,6,6-trimethylcyclohex-1-en-1-yl)nona-2,4,6,8-tetraen-1-yl)acetamide (3j, Ret-Gly): yield 23.7% (162 mg); $^1$H NMR (400 MHz, Acetone-d$_6$) δ 7.81 (s, 1H), 6.64 (dd, J=15.1, 11.2 Hz, 1H), 6.30 (d, J=15.1 Hz, 1H), 6.24-6.05 (m, 3H), 5.53 (t, J=6.9 Hz, 1H), 4.03 (dd, J=6.4, 5.3 Hz, 2H), 3.71 (s, 2H), 3.22 (s, 2H), 2.00 (t, J=6.2 Hz, 2H), 1.95 (s, 3H), 1.87 (s, 3H), 1.69 (s, 3H), 1.64-1.55 (m, 2H), 1.49-1.40 (m, 2H), 1.01 (s, 6H). $^{13}$C NMR (100 MHz, Acetone-d$_6$) δ 170.2, 138.2, 138.0, 137.1, 136.3, 135.5, 130.9, 129.3, 128.9, 126.3, 124.6, 54.3, 39.7, 36.7, 34.2, 33.0, 28.7, 21.4, 19.3, 12.2, 12.1. MALDI-TOF m/z [M]$^{•+}$ calcd. for C$_{22}$H$_{34}$N$_2$O: 342.267, found: 342.792.

(S)-2-(2-aminoacetamido)-N-((2E,4E,6E,8E)-3,7-dimethyl-9-(2,6,6-trimethylcyclohex-1-en-1-yl)nona-2,4,6,8-tetraen-1-yl)-3-methylbutanamide (3k, Ret-L-Val-Gly): yield 50.2% (443 mg); $^1$H NMR (400 MHz, Acetone-d$_6$) δ 8.06 (d, J=9.2 Hz, 1H), 7.73 (t, J=5.4 Hz, 1H), 6.64 (dd, J=15.1, 11.2 Hz, 1H), 6.29 (d, J=15.2 Hz, 1H), 6.24-6.03 (m, 3H), 5.53 (t, J=7.0 Hz, 1H), 4.38 (d, J=6.4 Hz, 1H), 3.96 (dd, J=10.9, 5.1 Hz, 2H), 3.74 (d, J=7.8 Hz, 2H), 2.00 (t, J=6.1 Hz, 2H), 1.94 (d, J=0.9 Hz, 3H), 1.86 (d, J=0.9 Hz, 3H), 1.68 (d, J=0.8 Hz, 3H), 1.62-1.56 (m, 2H), 1.50-1.41 (m, 2H), 1.01 (s, 6H), 0.90 (dd, J=10.8, 6.8 Hz, 6H). $^{13}$C NMR (100 MHz, Acetone-d$_6$) δ 170.73, 170.31, 138.17, 137.98, 137.05, 136.55, 135.53, 130.89, 128.89, 128.76, 126.34, 124.68, 57.56, 54.15, 39.66, 37.21, 34.21, 32.92, 31.84, 28.67, 21.35, 19.29, 19.09, 17.82, 12.15, 12.05. MALDI-TOF [M+Na]$^+$ calcd. for C27H$_{43}$N$_3$O$_2$Na: 464.325, found: 463.824.

(S)-2-amino-N-(2-(((2E,4E,6E,8E)-3,7-dimethyl-9-(2,6,6-trimethylcyclohex-1-en-1-yl)nona-2,4,6,8-tetraen-1-yl)amino)-2-oxoethyl)-3-methylbutanamide (3l, Ret-Gly-L-Val): yield 52.9% (467 mg); $^1$H NMR (400 MHz, CDCl$_3$) δ 8.07 (t, J=5.5 Hz, 1H), 7.09 (t, J=5.3 Hz, 1H), 6.57 (dd, J=15.1, 11.3 Hz, 1H), 6.29-6.01 (m, 4H), 5.46 (t, J=7.0 Hz, 1H), 3.99 (dd, J=15.2, 5.8 Hz, 4H), 3.25 (d, J=4.1 Hz, 1H), 2.28-2.16 (m, 1H), 2.01 (t, J=6.4 Hz, 3H), 1.95 (s, 3H), 1.90 (d, J=4.1 Hz, 3H), 1.84 (s, 3H), 1.71 (d, J=0.5 Hz, 3H), 1.65-1.56 (m, 2H), 1.48-1.43 (m, 2H), 1.30-1.25 (m, 1H), 1.02 (s, 6H), 0.97 (d, J=6.9 Hz, 4H), 0.83 (d, J=6.9 Hz, 3H). $^{13}$C NMR (100 MHz, CDCl$_3$) δ 175.6, 169.1, 138.0, 137.8, 137.4, 136.3, 136.2, 130.2, 129.4, 126.9, 126.9, 125.1, 60.3, 43.3, 39.8, 37.9, 34.4, 33.2, 31.3, 29.2, 22.0, 19.8, 19.5, 16.5, 12.9, 12.9. MALDI-TOF [M+Na]$^+$ calcd. for $C_{27}H_{43}N_3O_2Na$: 464.325, found: 463.810.

2-amino-N-(2-(((2E,4E,6E,8E)-3,7-dimethyl-9-(2,6,6-trimethylcyclohex-1-en-1-yl)nona-2,4,6,8-tetraen-1-yl)amino)-2-oxoethyl)acetamide (3m, Ret-Gly-Gly): yield 17.2% (137 mg); $^1$H NMR (400 MHz, Acetone-$d_6$) δ 8.28-8.09 (m, 1H), 7.77 (t, J=5.5 Hz, 1H), 6.63 (ddd, J=24.1, 15.1, 11.2 Hz, 1H), 6.26 (d, J=15.2 Hz, 1H), 6.21-6.00 (m, 3H), 5.49 (t, J=6.8 Hz, 1H), 3.97-3.88 (m, 2H), 3.85 (dd, J=3.9, 1.7 Hz, 1H), 3.37 (s, 2H), 3.30-3.20 (m, 2H), 2.70 (d, J=5.1 Hz, 2H), 1.98 (d, J=4.9 Hz, 2H), 1.93-1.91 (m, 3H), 1.82 (d, J=0.9 Hz, 3H), 1.62-1.54 (m, 3H), 1.50-1.38 (m, 2H), 1.25 (s, 2H), 0.98 (d, J=3.4 Hz, 6H). $^{13}$C NMR (100 MHz, Acetone-$d_6$) δ 171.1, 168.9, 138.2, 138.0, 137.1, 136.3, 135.4, 130.9, 129.0, 128.9, 126.3, 124.6, 54.2, 47.0, 39.7, 34.2, 32.9, 28.7, 26.8, 25.1, 21.4, 19.3, 12.2, 12.1. MALDI-TOF [M+Na]$^+$ calcd. For $C_{24}H_{37}N_3O_2Na$: 422.278, found: 421.688.

Results

Synthesis of Retinylamine Derivatives

Thirteen amino acid and peptide derivatives of retinylamine (3A-3M) were synthesized by conjugating selected amino acids or peptides as shown below. The structures of the derivatives are shown in Table 1.

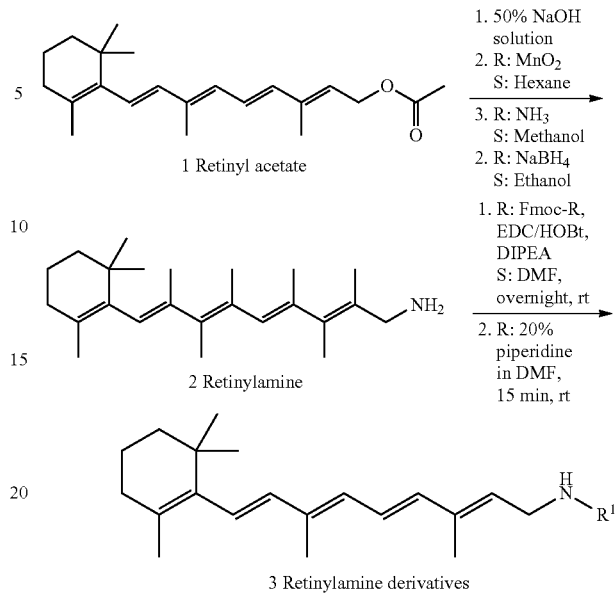

$R^1$ = L-Phenylalanine; L-Leucine; L-Isoleucine; L-Alanine; L-Proline; L-Valine; Glycine; β-Alanine; D-Alaline; D-Valine; Glycine-Glycine; L-Valine-Glycine; Glycine-L-Valine;

TABLE 1

| | Retinylamine derivatives | |
|---|---|---|
| No. Conjugates | Abbr | Structure |
| 3a Retinylamine-L-Alanine | Ret-L-ALa | |
| 3b Retinylamine-L-Leucine | Ret-L-Leu | |
| 3c Retinylamine-L-Isoleucine | Ret-L-Ile | |
| 3d Retinylamine-L-Valine | Ret-L-Val | |

TABLE 1-continued

Retinylamine derivatives

| No. | Conjugates | Abbr | Structure |
|---|---|---|---|
| 3e | Retinylamine-L-Phenylalanine | Ret-L-Phe | 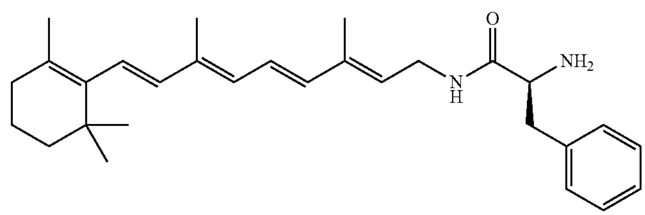 [SMILES: CC1=C(/C=C/C(C)=C/C=C/C(C)=C/CNC(=O)[C@@H](N)Cc2ccccc2)C(C)(C)CCC1] |
| 3f | Retinylamine-D-Alanine | Ret-D-Ala | 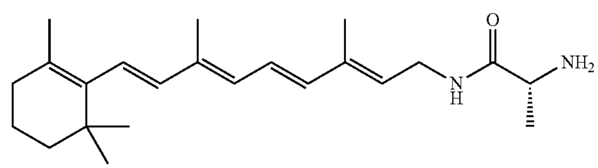 [SMILES: CC1=C(/C=C/C(C)=C/C=C/C(C)=C/CNC(=O)[C@@H](C)N)C(C)(C)CCC1] |
| 3g | Retinylamine-D-Valine | Ret-D-Val | 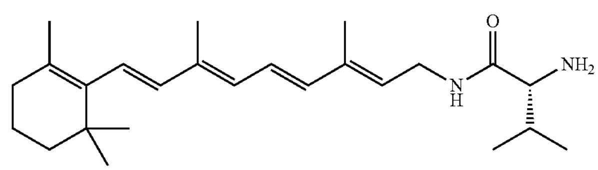 [SMILES: CC1=C(/C=C/C(C)=C/C=C/C(C)=C/CNC(=O)[C@H](N)C(C)C)C(C)(C)CCC1] |
| 3h | Retinylamine-β-Alanine | Ret-β-Ala | 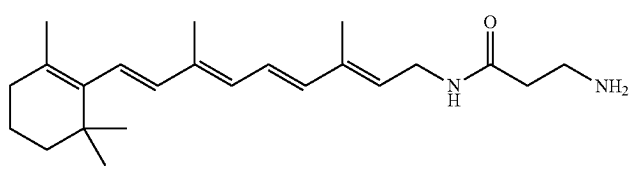 [SMILES: CC1=C(/C=C/C(C)=C/C=C/C(C)=C/CNC(=O)CCN)C(C)(C)CCC1] |
| 3i | Retinylamine-L-Proline | Ret-L-Pro | 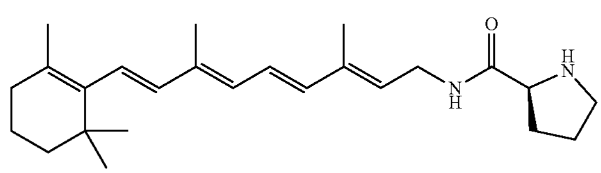 [SMILES: CC1=C(/C=C/C(C)=C/C=C/C(C)=C/CNC(=O)[C@@H]2CCCN2)C(C)(C)CCC1] |
| 3j | Retinylamine-Glycine | Ret-Gly | 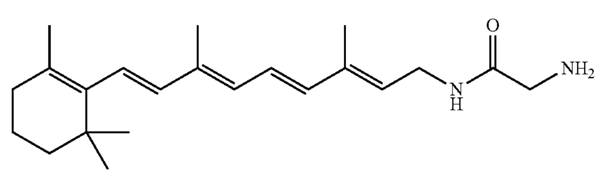 [SMILES: CC1=C(/C=C/C(C)=C/C=C/C(C)=C/CNC(=O)CN)C(C)(C)CCC1] |
| 3k | Retinylamine-L-Valine-Glycine | Ret-L-Val-Gly | 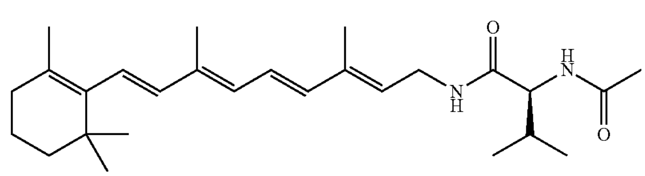 [SMILES: CC(=O)N[C@H](C(=O)NC/C=C(C)/C=C/C=C(C)/C=C/C1=C(C)CCCC1(C)C)C(C)C] |
| 3l | Retinylamine-Glycine-L-Valine | Ret-Gly-L-Val | 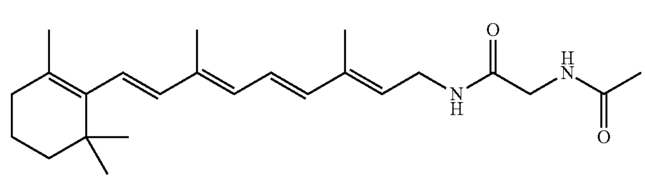 [SMILES: CC(=O)NCC(=O)NC/C=C(C)/C=C/C=C(C)/C=C/C1=C(C)CCCC1(C)C] |

TABLE 1-continued

Retinylamine derivatives

| No. | Conjugates | Abbr | Structure |
|---|---|---|---|
| 3m | Retinylamine-Glycine-Glycine | Ret-Gly-Gly | 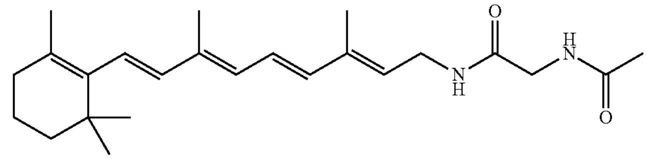 [SMILES: CC(=O)NCC(=O)NC/C=C(C)/C=C/C=C(C)/C=C/C1=C(C)CCCC1(C)C] |

The synthesis was straightforward, and Ret-NH$_2$ reacted with fluorenylmethyloxycarbonyl (Fmoc) protected amino acids or peptides in the presence of coupling agents. The Fmoc group then was removed using 20% piperidine in ethyl acetate solution to give target molecules. The retinylamine derivatives were characterized by 41-NMR, $^{13}$C-NMR and mass spectroscopy. The retinylamine derivatives had the purity over 95% as determined by HPLC except 3m Ret-Gly-Gly (RGG) with the purity of 90% (see SI). We tested the stability of RVG. Less than 5% degradation was observed when RVG was stored in the desiccator under vacuum at r.t. for 2 months, while 95% of Ret-NH$_2$ decomposed under the same condition within 1 week.

Effects on Light-Induced Retinal Degeneration

Figure 2:
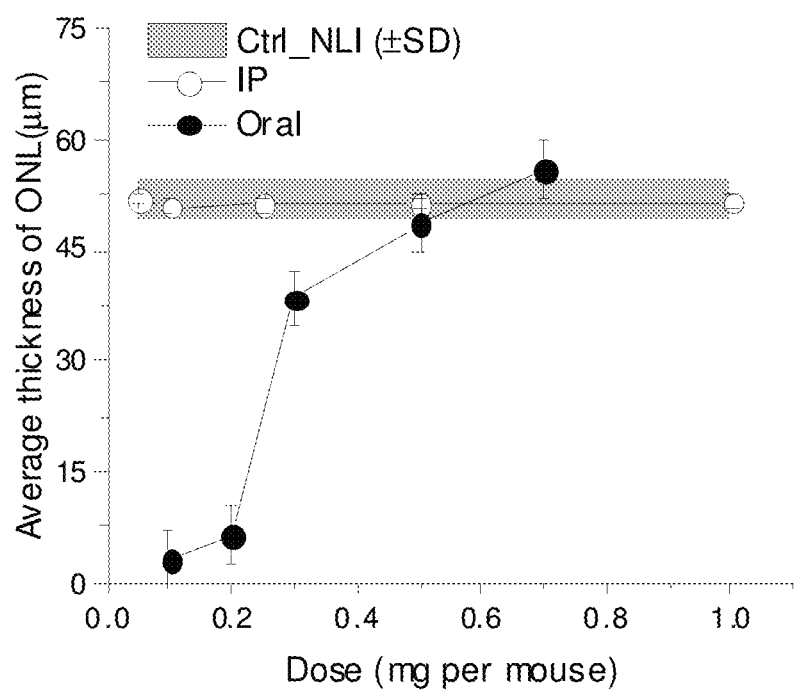
FIG. 2 illustrates a retinylamine dose-efficacy curve retinylamine administered to Abca4$^{-/-}$Rdh8$^{-/-}$ mice.
Figure 3:
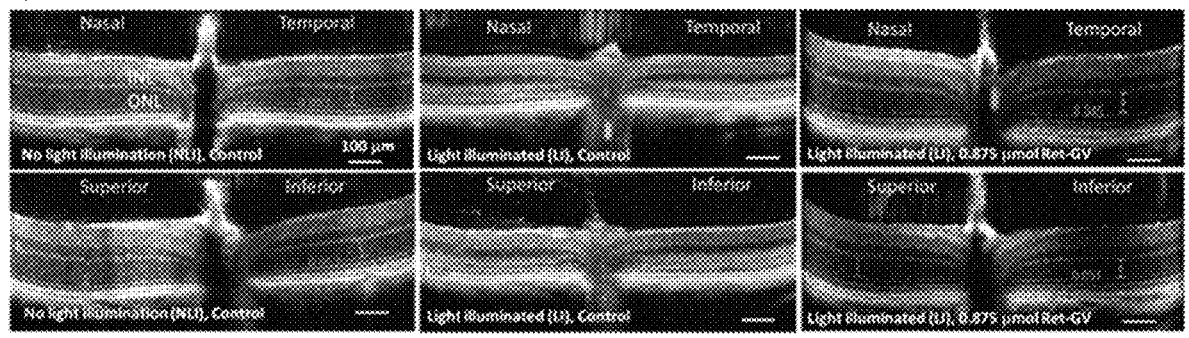
FIG. 3 illustrates OCT images indicate representative morphology of 4-week-old Abca4$^{-/-}$Rdh8$^{-/-}$ mice retinas.
Figure 4:
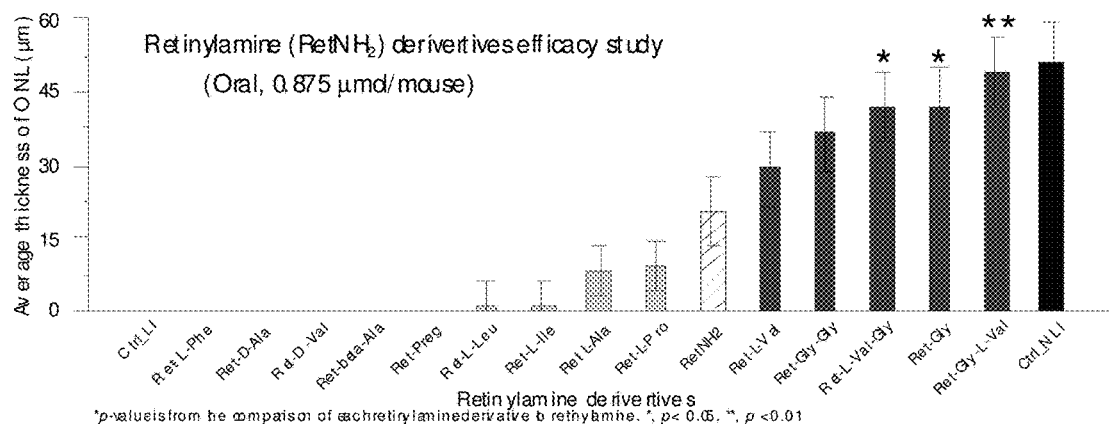
FIG. 4 illustrates a graph showing retinylamine derivatives in vivo efficacy study. ONL thicknesses were the average data measured from OCT images obtained 0.5 mm away from optical nerve at 4 locations (nasal, temporal, superior and inferior). Five mice were used for each treatment group. Statistical analyses were performed by the linear mixed-effects model with unstructured covariance structure fitted using SAS Proc Mixed software. Error bars indicate SE of the estimated means using a linear mixed-effects model.

The effectiveness of the retinylamine derivatives on preventing light-induced retinal degeneration was tested in four-week old Abca4$^{-/-}$Rdh8$^{-/-}$ mice according to the experimental scheme depicted in FIG. 1. After the mice were dark-adapted for 48 h, the drugs were gavaged at a dose 0.875 µmol/per mouse, which was selected based on the half protection dose for retinylamine after a dosing experiment, FIG. 2. Retinylamine was tested as a control at the same dose. Sixteen hours later, the mice were exposed to light at 10,000 lux for 1 h, and then kept in the dark for 3 days. Retinal integrity was assessed using optical coherence tomography (OCT). Representative OCT images of RVG, positive and negative controls are shown in FIG. 3. The mice without light illumination possessed intact retinas, and were used as a positive control. The mice without any treatment had photoreceptor cells completely destroyed after light illumination, and were used as a negative control. The retinal integrity was determined based on the thickness of outer nuclear layer (ONL) of the retinas measured from the OCT images. Reduced ONL thickness signifies the decreasing number of photoreceptors and retinal degeneration. The derivatives showed structural dependent therapeutic protection against light-induced retinal degeneration (FIG. 4). The glycyl, glycylvalyl and valylglycyl derivatives showed significantly better protection than Ret-NH$_2$ and other derivatives, with no visible retina damage at 4 locations around optic nerve. In comparison, the phenylalanyl, L-alanyl, L-leucyl, L-isoleucyl, L-prolyl, D-alanyl, D-valyl, β-alanyl, derivatives had little protecting efficacy under the testing condition. These results demonstrated that retinylamine derivatives of glycine and/or valine, especially RVG, RG, and RGV, showed significant improvement on preventing light-induced retinopathy over retinyl amine as a reduced dose.

Figure 5:
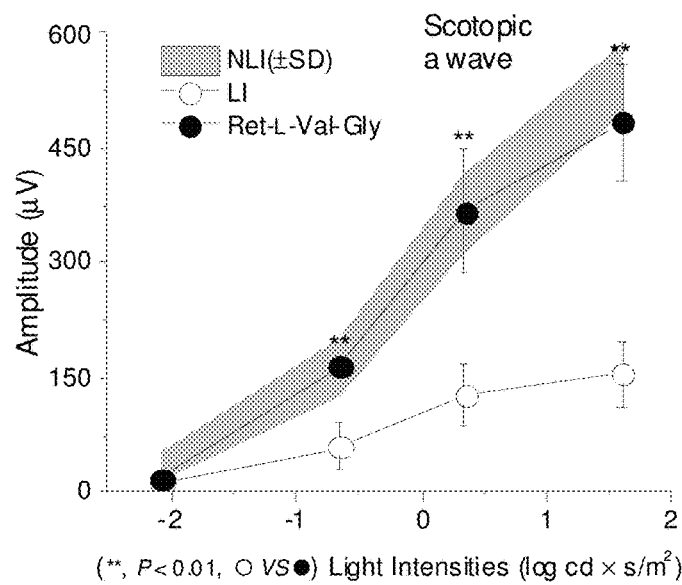
FIG. 5 illustrates a graph showing average ERG scotopic waves peak amplitudes of 4-week-old Abca4$^{-/-}$Rdh8$^{-/-}$ mice pretreated with RVG at a dose of 0.875 µmol per mouse 16 h prior to light illumination and evaluated 7 days later (NLI=no light illumination; LI=light illuminated). Error bars indicate S.D. of the means (n=3).
Figure 6:
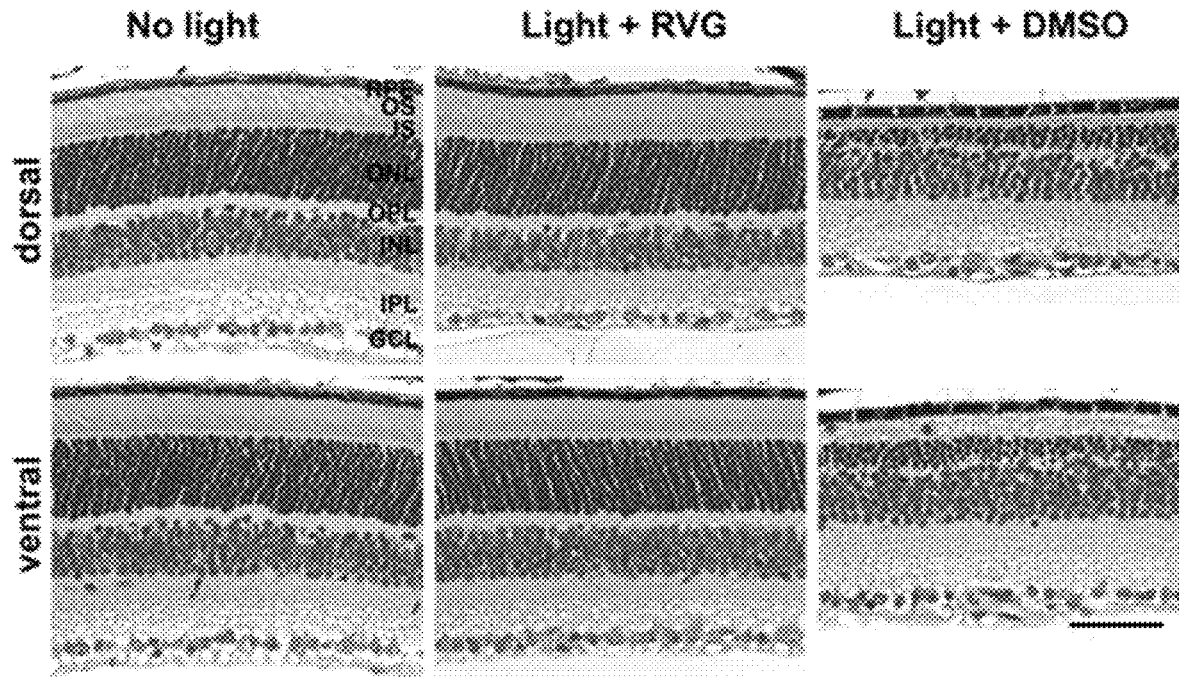
FIG. 6 illustrates images showing RVG protected Abca4$^{-/-}$Rdh8$^{-/-}$ retina from light damage. H&E staining of retinal sections through dorsal-ventral axis and across optic nerve head was performed 7 days after light exposure. The histology reveals light-induced retinal degeneration in vehicle (DMSO)-treated Abca4$^{-/-}$Rdh8$^{-/-}$ mouse which shows shortened outer nuclear layer. Administration of PG before light exposure prevents the retinal damage. RPE, retinal pigment epithelium; OS, outer segment; IS, inner segment; ONL, outer nuclear layer; OPL, outer plexiform layer; INL, inner nuclear layer; IPL, inner plexiform layer; GCL, ganglion cell layer. Scale bar: 50 µm.

The derivative RVG was selected as a lead agent for detailed in vitro and in vivo assessment because it was a solid at room temperature, while RG and RGV were oil although they showed similar efficacy. Solid materials are generally preferred for convenient formulation in drug development. Electroretinograms (ERGs) also were recorded to evaluate retinal function in these Abca4$^{-/-}$ Rdh8$^{-/-}$ mice after treatment for RVG followed by strong light exposure 16 h later. FIG. 5 shows average scotopic a wave ERG peak amplitudes of these mice in different treatment groups. ERG responses of mice treated with RVG and light illumination (LI) were virtually the same as those without light-illumination (NLI), while the average ERG peak amplitudes of the mice illuminated with strong light with no drug treatment were significantly lower. Histological analysis also showed that the mice treated with RVG maintained intact retina structure after exposure to intense light, while the retina of the mice without drug treatment had a thin ONL (FIG. 2).

Biodistribution in Normal C57BL Mice and LRAT$^{-/-}$ Mice

Figure 7:
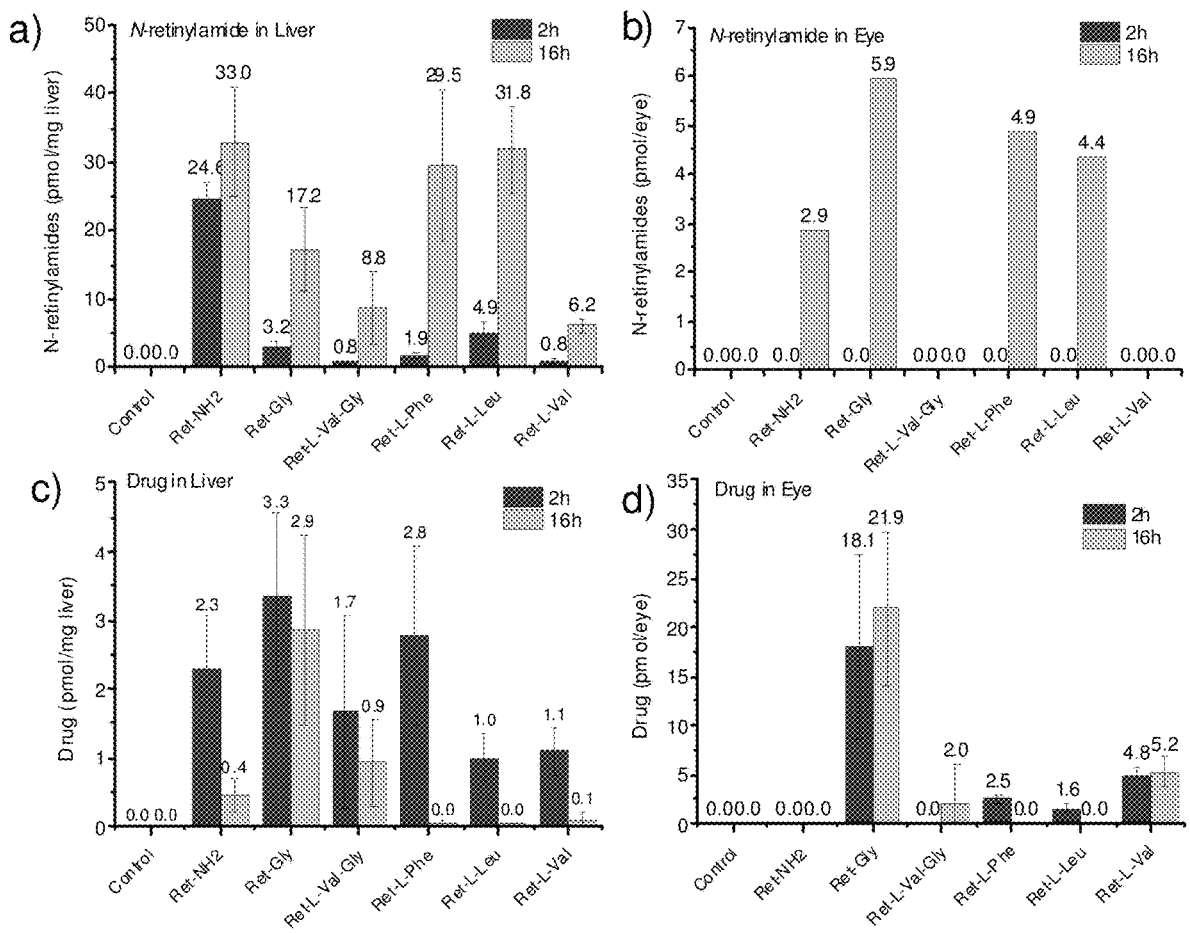
FIGS. 7(A-D) illustrate graphs showing biodistribution of N-retinylamides and retinylamine derivatives (Ret-Gly (RG), Ret-L-Val-Gly (RVG), Ret-L-Phe (RF), Ret-L-Leu (RL) and Ret-L-Val (RV)) in the liver, eye and blood after oral administration. The formulated drugs RG, RVG, RF, RL, RV or Ret-NH$_2$ 3.5 µmol per mouse) was orally gavaged into 4-week-old C57BL wild-type female mice. Mice then were sacrificed at predetermined time points (2 and 16 h) after such treatment. N-Retinylamides and drugs were extracted from the eyes, liver, blood and quantitatively determined by HPLC. Error bars indicate S.D. of the means (n=3).

Biodistribution of RVG and selected Ret-NH$_2$ derivatives with relatively high protecting effect, RG and RV, and low protecting effect, RF and RL in the liver and eye was determined after oral gavage in 4-week-old C57BL6 female mice to assess the biodistribution in the eye and to understand the structure and efficacy correlation. FIG. 7 shows the concentration of N-retinylamides, the main metabolites of Ret-NH$_2$, and the derivatives in the liver and eye at different time points (2 h and 16 h) after the gavage. The mice received Ret-NH$_2$ had much higher liver concentrations of N-retinylamides than those received the Ret-NH$_2$ derivatives at 2 h. The high liver concentrations of N-retinylamides suggest rapid absorption and metabolism of Ret-NH$_2$ after oral administration. No N-retinylamides were detected in the eye at 2 h for all treated mice. The concentration of N-retinylamides in the liver of all treated mice increased at 16 h post-treatment. Interestingly, the derivatives RVG, RG, and RV with high protecting effect had lower liver concentration of N-retinylamides than RF and RL, and RVG and RV had no detectable N-retinylamides in the eye. The derivatives RF and RL had comparable concentration of N-retinylamides in the eye as Ret-NH$_2$ at 16 h. The concentrations of the original drugs were also determined in the liver and eye at 2 h and 16 h (FIG. 7C, D). All tested drugs, including Ret-NH$_2$, were detected in liver and their concentrations decreased from 2 h to 16 h. The derivatives of RG and RV are detected in eyes at both 2 h and 16 h at a relatively high concentration. RVG was only detected at 16 h while RF and RL were only detected at 2 h. No free Ret-NH$_2$ was detected in the eye, possibly due to rapid metabolism or binding to RPE65. The results indicate that RF and RL were rapidly metabolized into inactive N-retinylamides in the eye, and RV and RV were stable against metabolism and had prolonged presence in the eye as intact drug molecules.

In Vitro Caco-2 Cell Transport and ARPE-19 Cell Uptake

Figure 8:
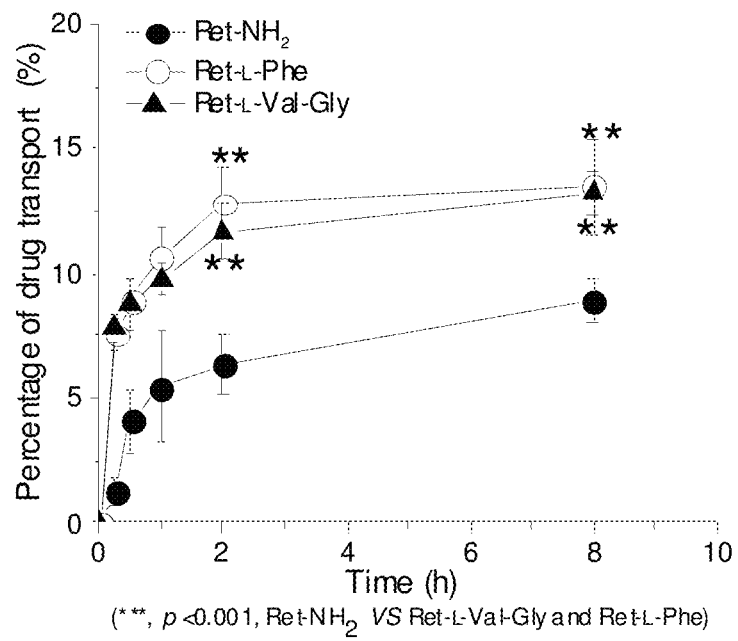
FIG. 8 illustrates a plot showing drug (Ret-NH$_2$, RVG and RF) transport through Caco-2 cell mono-layer. A mono-layer of Caco-2 cells is grown on a filter separating two stacked micro well plates into apical chamber (AP) and basolateral chamber (BL). The permeability of drugs through the cells is determined after the introduction of a drug AP side of the filter and using UV monitoring the drug concentration in BL side.
Figure 9:
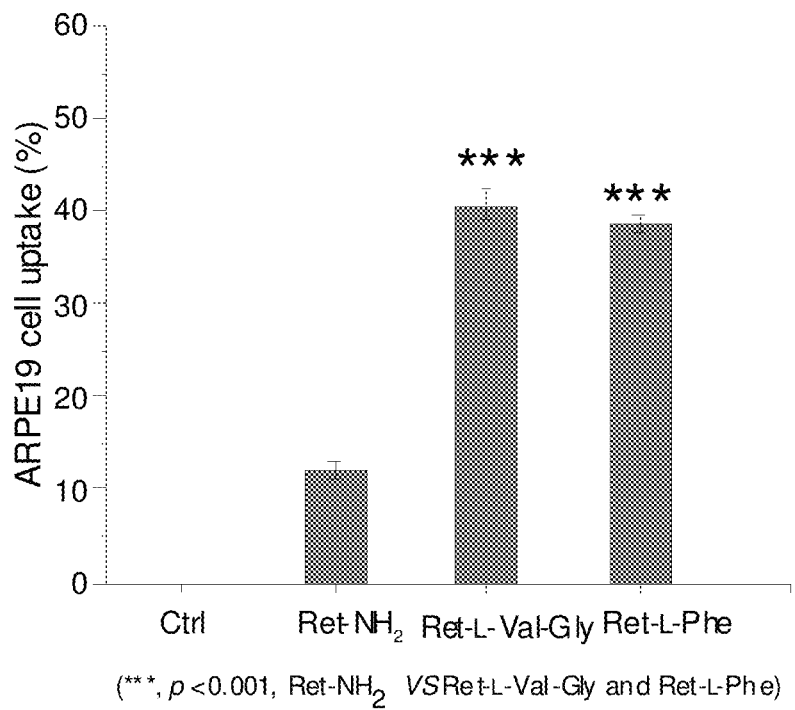
FIG. 9 illustrates a graph showing drug uptake into ARPE19 cells. After co-incubation ARPE19 cells and selected drugs (RVG, RF) for 16 hs, medium was removed and cells were then collected. Drug was extracted from cell and analyzed by HPLC.

The structural effect on transport and cell uptake was investigated with RVG, RF and Ret-NH$_2$ in Caco-2 cells, human epithelial colorectal adenocarcinoma cell monolayer as an in vitro model for oral gastrointestinal transport, and ARPE19 cells, modified human RPE cell, for cellular uptake. As shown in FIGS. 8 and 9, both RVG and RF exhibited significantly higher transport through the Caco-2 monolayer and higher uptake in ARPE19 cells than Ret-$NH_2$. There was no significant difference between RVG and RF in both cases. The results indicate that modification of Ret-$NH_2$ with the amino acid or peptide facilitated the transport and cellular uptake through the peptide transporters.

Effects on the Retinoid Cycle

Figure 10:
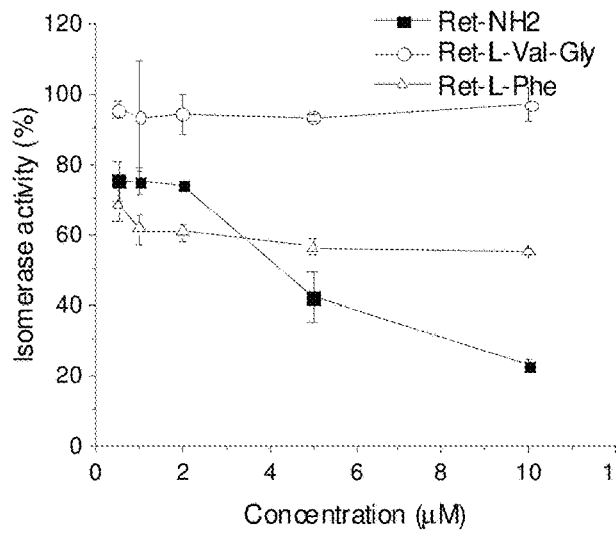
FIG. 10 illustrates a plot showing inhibition of 11-cis-retinol production by retiylamine derivatives (RVG and RF). RPE microsomes were incubated for 1 h with each compound tested at a concentration of 0.5 to 10 µM addition of 10 µM all-trans-retinol and RPE microsomes.
Figure 11:
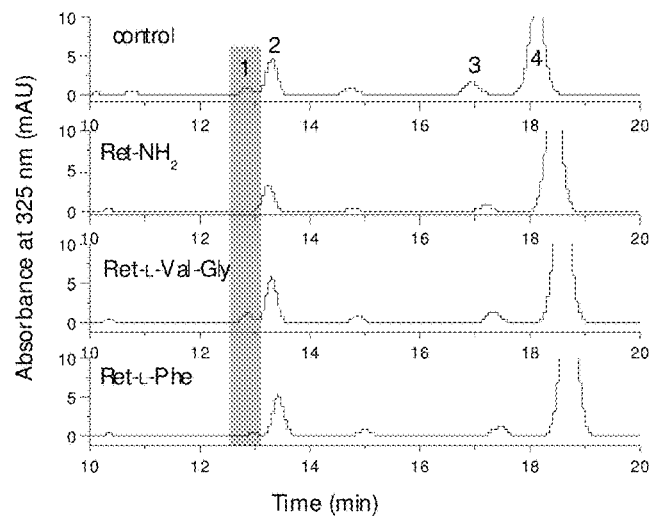
FIG. 11 illustrates a plot showing the results of NIH3T3 cells culture experiment. Cells were incubated with 10 µM all-trans-retinol in addition to 4.5 µM of each tested drugs (Ret-NH$_2$, RVG and RF) in growth medium for 16 h prior to organic extraction. Supplementation of the growth medium with 3 µM Ret-NH2 resulted in nearly complete inhibition of 11-cis-retinol production, RVG had no significant effect on this activity. Peaks were identified based on elution time and absorbance spectra that were identical with synthetic standards (1, 11-cis-retinol; 2, 13-cis-retinol; 3, 9-cis-retinol; 4, all-trans-retinol).

The effect of RVG on the regeneration of 11-cis-retinol in the retinoid cycle was investigated in vitro by incubating the drug and RPE microsomes with Ret-$NH_2$ and RF as controls. Their activity of RPE65-dependent retinoid isomerization in the presence of all-trans-retinol and the 11-cis-retinoid binding protein, retinaldehyde-binding protein was determined based on the 11-cis-retinol production by HPLC. FIG. 10 shows the concentration dependent inhibition of RPE65 on 11-cis-retinol production in the presence of RVG, RF, and Ret-$NH_2$. Ret-$NH_2$ showed concentration dependent inhibition of RPE65 and RF resulted in partial inhibition, but not in a concentration dependent manner RVG did not show significant inhibition as compared to the untreated control up to 10 μM. Similar results were obtained during the incubation of NIH3T3 cells stably expressing LRAT and RPE65 in the presence of 10 μM all-trans-retinol and 4.5 μM of Ret-$NH_2$, RVG or RF. Concentration of 11-cis-retinoids was determined by HPLC at 16 h after cell homogenization, saponification, and retinoid extraction, FIG. 11. Production of 11-cis-retinol was measured in nontreated cells (control), whereas the addition of Ret-$NH_2$ inhibited isomerase activity and 11-cis-retinol production. RF showed partial inhibition of 11-cis-retinol production. RVG had no significant inhibitive effect on this activity.

Figure 12:
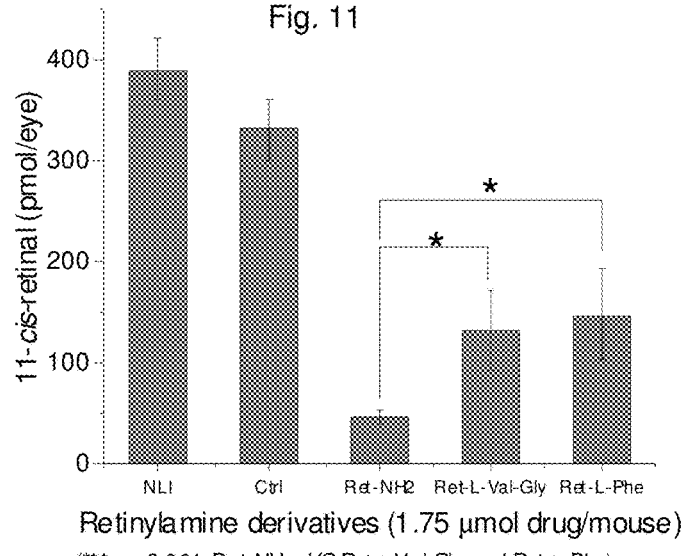
FIG. 12 illustrates a graph comparing 11-cis-retinal regeneration in mice treated with selected retinylamine derivatives. Dark-adapted C57BL/6J mice were given the shown dose of inhibitor by oral gavage 16 h before they received a bleach for 10 min at 7000 lux. Regeneration of 11-cis-retinal continued for 24 h in the dark, after which ocular retinoids were extracted and separated by normal phase HPLC.

The inhibitive effective on RPE65 was further investigated in dark-adapted C57BL/6J wild-type mice after RF or RVG oral gavage at a dose of 1.75 μmol per mouse 16 h prior to photo-bleach (7000 lux, 10 min). FIG. 12 shows the regeneration of 11-cis-retinal in the eye as quantified with HPLC. The mice treated with Re—$NH_2$ had a much lower concentration of 11-cis-retinal than the untreated controls, indicating slow regeneration of 11-cis-retinal and strong inhibitive effect of the drug in the retinoid cycle. Both RVG and RF resulted in faster regeneration of 11-cis-retinal in the eye, and weaker inhibition of retinoid cycle than Ret-$NH_2$.

In Vitro Schiff Base Formation with atRAL

The above experiments revealed that RVG reduced 11-cis-retinal concentration in the eye, but did not inhibit the activity of RPE65. We hypothesized the Ret-$NH_2$ and its amino acid and peptide derivatives could also act as scavengers to sequester atRAL by forming Schiff base conjugates, which could slow down retinoid cycle and reduce the production of 11-cis-retinal. We next assessed the ability of RVG and RF to form Schiff base with atRAL. FIG. 13 shows the HPLC chromatograms, UV-vis, and mass spectra of the reaction mixture of Ret-$NH_2$, RF or RVG (0.2 mM) with all-trans-retinal in ethanol 2 h at room temperature. The result showed that all drug compounds were able to form Schiff base with atRAL.

Effects on Retinal Function

Strong inhibition of retinoid cycle could cause temporary vision impairment. Electroretinograms (ERGs) were recorded to in retinal function in C57BL/6.1 wild-type mice at 6 and 24 h after oral gavage of RVG, RF or Ret-$NH_2$ at a dose of 1.75 μmol per mouse. The preliminary results showed that no significant ERG signal was detected in the retina of the mice treated with Ret-$NH_2$ in first 24 h after the treatment, indicating temporary impairment of retina function. RVG and RF resulted in attenuated ERG signal as compared with that of the nontreated control at 6 h post-treatment. ERG signal in the mice treated with RVG and RF then recover to the magnitude of the untreated control mice at 24 h post treatment. The results suggest that RVG and RF have much less side effects on retina function or vision than the Ret-$NH_2$.

In summary, we synthesized and tested several retinylamine derivatives of amino acids and dipeptides. These chemically modified retinylamine derivatives possessed improved structural stability, sequestered toxic atRAL by forming Schiff base. The derivatives showed structural dependent efficacy in preventing light-induced retinal degeneration in $Abca4^{-/-}Rdh8^{-/-}$ mice. The derivatives containing glycyl and/or L-valyl residues demonstrated higher therapeutic efficacy than retinylamine and other tested amino acid derivatives. The high efficacy of the glycyl, L-valyl, and glycylvalyl derivatives was correlated to relatively high stability against metabolism in the eye. The derivative RVG with better combination of pharmaceutical and pharmacological properties is identified as a lead therapeutic agent. RVG provides effective protection against retinal degeneration, does not inhibit RPE65 protein, and results in minimal interference of retinoid cycle chemistry. The mice treated with RVG had rapid regeneration of 11-cis-retinal and recovery of retina function. RVG is a promising therapy for prophylactic prevention of human retinopathy with minimal side effects.

Example 2

We employed polyethylene glycol (PEG) with functionalized side chains as our drug carrier and synthesized a polymer conjugate of Ret-$NH_2$ with the peptide spacer, glycine-phenylalanine-leucine (GFL). PEG is one of the most commonly used biocompatible polymers used in drug delivery. It has been employed as a vehicle, additive or an excipient in food, cosmetics and pharmaceuticals approved by U.S. Food and Drug Administration (FDA). With a molecular weight higher than 4 kDa, PEG is not appreciably absorbed from rat intestine for at least 5 h after administration. PEG with functionalized side chains can increase drug loading efficiency per polymer chain. After oral gavage, the pharmacokinetics and the effectiveness of the resulting conjugate for preventing acute light-induced retinal degeneration were determined in mice, including the $Abca4^{-/-}Rdh8^{-/-}$ mouse model.

Materials and Methods

Materials and Equipment

All commercially available reagents and solvents were received as analytically pure substances. Polyethylene glycol with eight side-chain propionic acid groups (PEG-BPA, MW=20,000 g/mol) was obtained from Sunbio, Inc. (Anyang City, South Korea). Benzotriazol-1-yl-oxytripyrrolidinophosphonium hexafluorophosphate (PyBOP), 1-hydroxybenzotriazole hydrate (HOBt), 2-chlorotrityl chloride resin and Fmoc-protected amino acids were purchased from Chem-Impex International, Inc (IL, USA). Anhydrous N,N-diisopropylethyl amine (DIPEA), p-nitrophenol and N,N-dimethylformamide (DMF) were obtained from Sigma-Aldrich Co., LLC. 4-Dimethylaminopyridine (DMAP), N,N'-diisopropylcarbodiimide (DIC) and trifluoroacetic acid (TFA) were from Oakwood Products, Inc (SC, USA).

Chemical reactions were monitored by thin-layer chromatography (TLC) on silica gel plates (60 $F_{254}$) with a fluorescent indicator at 254 nm. Intermediates and Ret-NH$_2$ derivatives were purified by column chromatography on silica gels (Silica gel grade: 200-400 mesh, 40-63 μm) and characterized by $^1$H NMR spectroscopy and matrix-assisted laser desorption/ionization time-of-flight (MALDI-TOF) mass spectrometry. Proton-NMR spectra were recorded on a Varian 400 MHz NMR spectrometer. MALDI-TOF mass spectra were acquired on a Bruker Autoflex III MALDI-TOF MS in a linear mode with 2,5-dihydroxybenzoic acid (2,5-DHB) as a matrix.

Animal Models

Abca4$^{-/-}$Rdh8$^{-/-}$ mice were obtained as previously described. Mice were housed and cared in the animal facility at the School of Medicine, Case Western Reserve University according to an animal protocol approved by the CWRU Institutional Animal Care and Use Committee and conformed to recommendations of the American Veterinary Medical Association Panel on Euthanasia and the Association of Research for Vision and Ophthalmology.

Solid-Phase Synthesis of Peptide NH$_2$-GFL-OH

The peptide spacer NH$_2$-GFL-OH was synthesized using standard solid-phase Fmoc peptide synthesis. 2-Chlorotrityl chloride resin was first reacted with Fmoc-Leu-OH and addition of the remaining amino acids was accomplished by repeated cycles of coupling and deprotection. Fmoc-amino acids (2-fold molar excess) were coupled to the resin in the presence of the condensation reagents, PyPOP and HOBt. The peptide was obtained after cleavage from the resin with TFA (95%) with a yield of 60%. $^1$H NMR (400 MHz, D$_2$O, ppm): 8.43 (d, J=7.8 Hz, 1H, —CONH—), 7.47-7.11 (m, 5H, —CH$_2$C$_6$H$_5$), 4.73-4.54 (m, 1H, —NHCHCO—), 4.31 (dd, J=9.0, 5.8 Hz, 1H—NHCHCO—), 3.73 (q, J=16.3 Hz, 2H, NH$_3^+$CH$_2$—), 3.04 (ddd, J=22.1, 13.9, 7.5 Hz, 2H, —CH$_2$C$_6$H$_5$), 1.72-1.41 (m, 3H, —CH$_2$CH(CH$_3$)$_2$), 0.84 (dd, J=19.0, 6.1 Hz, 6H, —CH(CH$_3$)$_2$). MALDI-TOF (m/z, M$^+$) calculated for C$_{17}$H$_{25}$N$_3$O$_4$ was 335.185; found was 335.649.

Synthesis of the PEG-GFL-NH-Ret Conjugate

PEG-8PA (5 g, 2 mmol propionic acid) was dissolved in 100 mL dichloromethane, and 0.84 g (6 mmol) p-nitrophenol, 75 mg (0.6 mmol) 4-dimethylaminopyridine (DMAP) and 0.76 g (6 mmol) N,N'-diisopropylcarbodiimide (DIC) were added to the solution. The reaction mixture was stirred for 24 h at room temperature, and then dropped into ether. The solid was collected and washed three times with ether to obtain PEG-8(PA-ONp), yield 91.9% (4.82 g). PEG-8 (PA-ONp) (4 g, 1.6 mmol ONp active ester) was dissolved in 30 mL dimethyl sulfoxide and 880 mg (1.96 mmol) H$_2$N-Gly-Phe-Leu-OH·TFA and 1 mL DIPEA were added to the solution. The reaction mixture was stirred for 24 h at room temperature, and then dripped into ether. The resulting solid was collected and washed three times with ether to obtain PEG-8(PA-GFL-OH), yield 92.7% (4.0 g). $^1$HNMR (400 MHz, Acetone-d$_6$)$^1$H NMR (400 MHz, acetone-d$_6$, ppm): 7.26 (bm, 5H, —CH$_2$C$_6$H$_5$), 4.72 (s, 1H), 4.48 (s, 1H), 3.80-3.34 (m, 184H, —OCH$_2$CH$_2$O— and PEG-CH$_2$CH$_2$CONH), 3.21 (m, 1H), 2.96 (m, 1H), 1.64 (m, 3H), 1.01-0.81 (m, 6H, —CH(CH$_3$)$_2$).

PEG-8(PA-GFL-OH) (2.12 g, 0.8 mmol GFL) was dissolved in 30 mL dichloromethane, and 336 mg (2.4 mmol) p-nitrophenol, 30 mg (0.24 mmol) DMAP and 302 mg (2.4 mmol) DIC were added to the solution. The reaction mixture was stirred for 24 h at room temperature, and dripped into ether. The solid was collected and washed three times with ether to give PEG-8(PA-GFL-ONp), yield 94.3% (2.05 g). PEG-8(PA-GFL-ONp) (2.15 g, 0.8 mmol ONp active ester) was then dissolved in 30 mL dimethyl sulfoxide, and 570 mg (2 mmol) Ret-NH$_2$ and 0.5 mL DIPEA were added to the mixture. The reaction mixture was stirred for 24 h at room temperature, and dripped into ether. The solid was collected and washed three times with ether, yield 70.6% (1.68 g). About 4 drug molecules on average were conjugated to each PEG$_{20k}$ (5.7 w/w) as calculated from the $^1$H NMR spectrum. $^1$H NMR (400 MHz, DMSO-d$_6$, ppm): 7.19 (bm, 5H, —CH$_2$C$_6$H$_5$), 6.09 (bm, 1H, —CH=CH—), 4.53 (s, 1H), 4.26 (s, 1H), 3.91-3.09 (m, 165H, —OCH$_2$CH$_2$O— and PEG-CH$_2$CH$_2$CONH), 3.04-3.01 (bm, 2H), 2.76 (s, 1H), 1.98-1.81 (bm, 3H), 1.59 (bm, 8H), 0.99 (m, 3H, —C(CH$_3$)$_2$), 0.85 (m, 6H, —CH(CH$_3$)$_2$).

Pharmacokinetics of PEG-GFL-NH-Ret in C57BL Mice

Female C57BL mice (4-week-old) were randomly divided into two dosing groups. One group of mice was gavaged with one dose of Ret-NH$_2$ (1 mg per mouse, dissolved in DMSO), and the other group of mice was also gavaged once with PEG-GFL-NH-Ret (17.5 mg per mouse, equivalent to 1 mg Ret-NH$_2$ per mouse). Then at each predetermined time point (0, 4 h, 8 h, 24 h, 48 h and 72 h after drug administration), 6 mice were sacrificed. The liver and eye balls were collected to determine tissue N-retinylamide content for pharmacokinetic analysis. A portion of the liver tissue (ca. 0.5 g) was weighed, homogenized in 2 mL 1:1 ethanol:PBS solution and the eye balls were similarly processed. N-Retinylamides were extracted in 4 mL hexane, concentrated, and reconstituted to a 300 μL volume. Normal-phase HPLC (Agilent-Zorbax SIL; 5 μm; 4.5×250 mm; flow rate of 1.4 mL/min; 80:20 hexane:ethyl acetate (v:v); detection at 325 nm) was utilized to determine N-retinylamide concentration in these tissues.

Preventing Light-Induced Retinal Degeneration with PEG-GFL-NH-Ret in Abca4$^{-/-}$Rdh8$^{-/-}$ Mice Abca4$^{-/-}$Rdh8$^{-/-}$ mice (male and female, 4-week-old, 4-5 mice in each treatment group) were kept in the dark for 48 h before each experiment. Then free Ret-NH$_2$ (0.5 mg, 1.75 μmol) per mouse) or conjugate PEG-GFL-NH-Ret (8.75 mg per mouse, equivalent to 0.5 mg free Ret-NH$_2$ per mouse) was administered by gastric gavage. Mice were illuminated with 10,000 lux light for 30 min at 1 day, 3 days or 6 days after their gavage, and then kept in the dark for 7 days when final retinal evaluations were performed. Mice were anesthetized by intraperitoneal injection of a cocktail (20 μL/g body weight) containing ketamine (6 mg/mL) and xylazine (0.44 mg/mL) in PBS buffer (10 mM sodium phosphate, and 100 mM NaCl, pH 7.2. Pupils were dilated with 0.01% tropicamide. Retinas of mice were imaged in vivo with ultra-high resolution spectral-domain OCT (SD-OCT; Bioptigen, Irvine, Calif.). Five pictures acquired in the B-scan mode were used to construct each final averaged SD-OCT image. Quantitative ONL thicknesses were measured from OCT images along the vertical meridian from the superior to inferior retina. Electroretinograms (ERGs) were then recorded as previously reported 24 h after the OCT test. Dark-adapted mice were anesthetized by the same protocol used for OCT recordings. All experimental procedures were performed under a safety light. A contact lens electrode was placed on the eye, and a reference electrode and ground electrode were placed underneath the skin between the two ears and in the tail, respectively. ERGs were recorded with the universal electrophysiologic system UTAS E-3000 (LKC Technologies, Inc., Gaithersburg, Md.). Light intensity calibrated by the manufacturer was computer-controlled. Mice were placed in a Ganzfeld dome, and scotopic responses to flash stimuli were obtained from both eyes simultaneously.

Results
Synthesis of PEG-GFL-NH-Ret Conjugates

PEG-GFL-NH-Ret conjugates were synthesized from 20 kDa polyethylene glycol with eight propionic acid side chains (PEG-8-PA) as shown below.

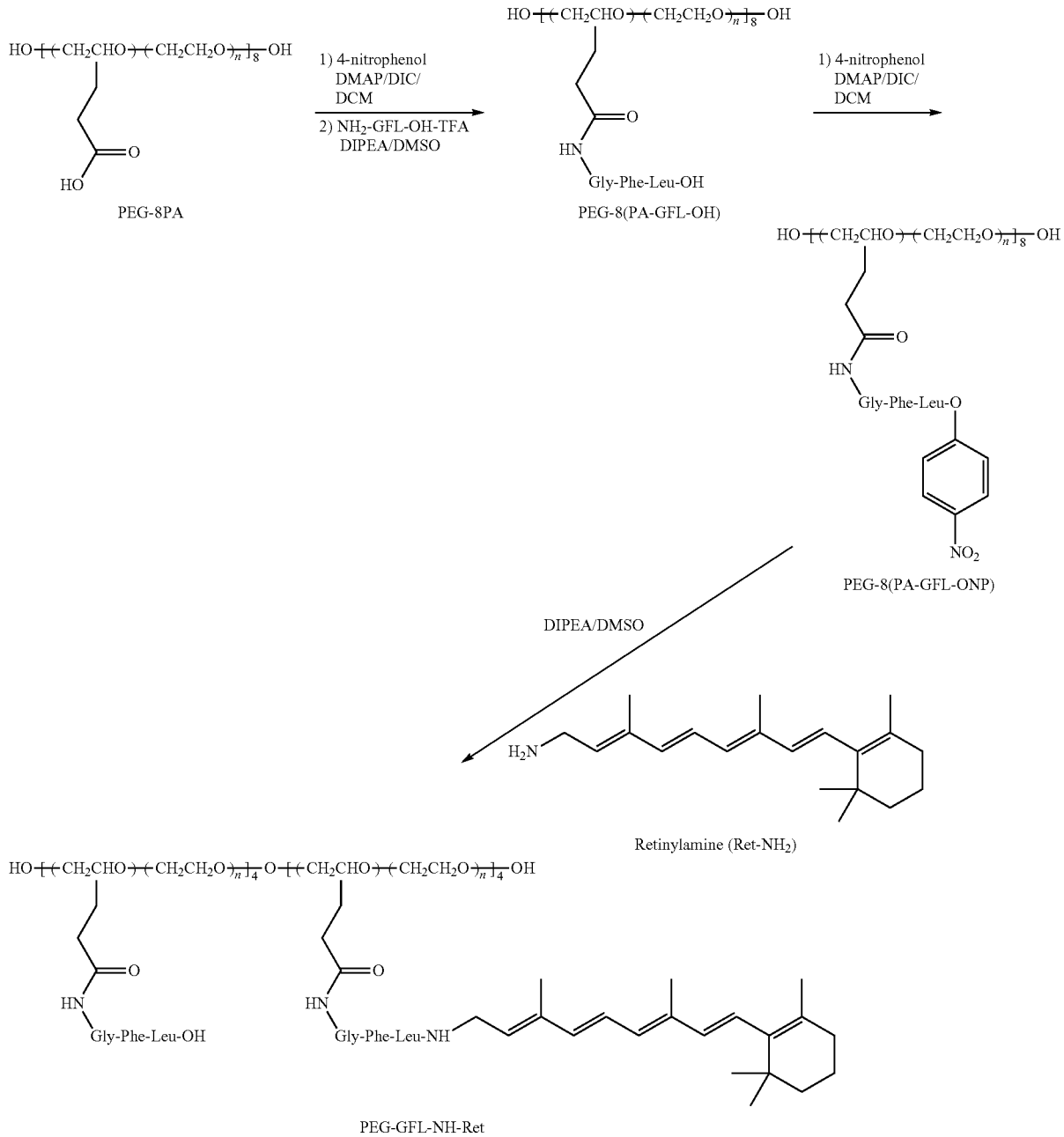

The peptide spacer $NH_2$-Gly-Phe-Leu-OH ($NH_2$-GFL-OH) was synthesized according to standard solid-phase peptide chemistry with a 60% yield. PEG-8PA was first converted to PEG-8PA p-nitrophenol active ester by reaction with excess p-nitrophenol in the presence of coupling agents. GFL peptide was then incorporated into the PEG side chains with an excess of peptide to ensure complete conjugation. The resulting PEG-8(PA-GFL-OH) was then reacted with excess p-nitrophenol in the presence of coupling agents to yield PEG-8(PA-GFL-ONp) active ester. The polymer Ret-$NH_2$ conjugate was prepared by reacting PEG-8(PA-GFL-ONp) with Ret-$NH_2$ and drug loading was controlled by the molar ratio of the two components. All intermediates were characterized by analytic HPLC, $^1H$ NMR spectroscopy and MALDI-TOF mass spectrometry. Because PEG conjugates with more than 4 Ret-$NH_2$ molecules per polymer chain exhibited poor water solubility, the conjugate with 4 molecules of Ret-$NH_2$ on average was selected for in vivo experiments. The final product, namely PEG (GFL-NH-Ret)$_4$ was characterized by $^1H$ NMR spectroscopy.

The number and weight-average molecular weights of polymer conjugate was 21 and 22 kDa (Mw/Mn=1.05), as determined by size exclusion chromatography. The stability of drug Ret-NH$_2$ has greatly improved after conjugation. The structure of PEG-GFL-NHRet was preserved during the storage in solid form more than 6 months at room temperature, while free Ret-NH$_2$ decomposed in less than 1 week under the same condition.

Pharmacokinetics of PEG-GFL-NH-Ret in Normal C57BL Mice

Pharmacokinetic distribution of Ret-NH$_2$ in the liver and eye was determined after oral gavage of PEG-GFL-NH-Ret compared with free Ret-NH$_2$ at the same equivalent dose of 1 mg (3.5 µmol) Ret-NH$_2$ per mouse into 4-week-old C57BL6 female mice. FIGS. 14(A-B) show the concentration of N-retinylamides, the main metabolites of Ret-NH$_2$, in the liver (A) and eye (B) at different time points after the gavage. Mice treated with free Ret-NH$_2$ had much higher liver concentrations of N-retinylamides than those treated with the conjugate, especially in the first 8 h after the gavage. The high liver concentrations of N-retinylamides suggest rapid absorption and metabolism of Ret-NH$_2$ after oral administration. In contrast, liver concentrations of N-retinylamides in mice treated with PEG-GFL-NH-Ret were below the detection limit in the first 4 h after conjugate administration and then were maintained at a stable low level from 8 h to 72 h thereafter. Both the conjugate and free Ret-NH$_2$ resulted in similar concentrations of N-retinylamides in the eye (P>0.05) under the same conditions. The liver is a major first pass organ for drug absorption after oral administration. The pharmacokinetics in the liver indicates that the PEG conjugate could control the sustained drug release from the conjugate after oral administration; drug release from the conjugate was slow initially and then was maintained at a stable low rate for up to 72 h. The low concentrations of N-retinylamides found in the liver after conjugate administration are advantageous for minimizing potential toxic side effects associated with the drug. Although concentrations of N-retinylamides in the liver were substantially higher after gavage with free retinylamine than the conjugate, both resulted in comparable concentrations of N-retinylamides in the eye over the 3 day experimental period. The result demonstrated that PEG-GFL-NH-Ret was effective in delivering sufficient Ret-NH$_2$ into the eyes while maintaining low drug concentrations in the rest of the body.

In Vitro Drug Release Studies

Free Ret-NH2 is highly unstable and it was difficult to accurately determine the drug release kinetics by incubating PEG-GFL-NH-Ret with the digestive enzymes from the GI tract. In order to accurately assess the drug release kinetics, a model drug p-nitroaniline (pNA) conjugate, PEG-GFL-pNA, was synthesized by reacting PEG-8(PA-GF-ONP) with Leu-pNA. FIGS. 15(A-B) show the in vitro drug release kinetics of p-nitroaniline (pNA) from PEGGFL-pNA and Leu-pNA in the presence of the homogenates of rat intestinal brush border in isotonic phosphate buffer at pH 6.8 assayed by HPLC. The HPLC elution times for pNA released from PEG-GFL-pNA and Leu-pNA were both 4.37 min consistent with the retention time of the pNA standard (4.38 min) (FIG. 15B). At 16 h after the incubation, 28.1 and 97.2% free pNA was released from PEG-GFL-pNA and LeupNA, respectively. The polymer conjugate PEG-GFL-pNA showed a more controllable release pattern compared to the low-molecular-weight amino acid conjugate Leu-pNA.

Effects of PEG-GFL-NH-Ret on Preventing Light-Induced Retinal Degeneration

The therapeutic efficacy of PEG-GFL-NH-Ret in preventing light-induced retinal degeneration was investigated in 4-week-old male and female hybrid Abca4$^{-/-}$Rdh8$^{-/-}$ mice. Both Abca4 and Rdh8 are the key enzymes of the visual cycle that act on atRAL. Bright white light induces photoreceptor cell death and retinal degeneration, signs similar to human STGD/AMD disease, in this mouse model. As compared to free Ret-NH$_2$, sustained release of Ret-NH$_2$ from PEG-GFL-NH-Ret in the GI tract after oral administration could provide prolonged protection against light induced retinal degeneration in these double knockout mice. FIG. 16 shows a schematic representation of our experimental design. The effectiveness of the conjugate for prolonged retinal protection was determined after the exposure of 4-week-old Abca4$^{-/-}$Rdh8$^{-/-}$ mice to 10,000 Lux light for 30 min at 1, 3 and 6 days after a single oral administration of either 8.75 mg of PEG-GFL-NH-Ret or the equivalent 0.5 mg free Ret-NH$_2$ per mouse.

Retinal integrity of the treated mice was determined with ultra-high resolution spectral-domain optical coherent tomography (OCT). FIG. 17 shows representative OCT images of retinas from mice in different treatment groups. Free Ret-NH$_2$ produced effective protection against light-induced retinal degeneration when gavaged at a dose of 0.5 mg/mouse 1 day before light exposure but did not maintain such protection when administered 3 days before the same exposure. In contrast, PEG-GFL-NH-Ret gavaged 3 days before light exposure did provide such protection at the same equivalent dose. No protective effect against light-induced retinal degeneration was imaged by OCT after pretreatment with either free Ret-NH$_2$ or PEG-GFL-NH-Ret 6 days before light exposure. FIGS. 18(A-B) show the thicknesses of the outer nuclear layer (ONL) of retinas measured from OCT images of mice in the different treatment groups. Both the free drug and PEG-GFL-NH-Ret gavaged 1 day before light exposure similarly protected the ONL against strong light with a thickness comparable to that of mice without light illumination. The retinal ONL thickness of mice treated with conjugate 3 days before strong light illumination remained the same as that of un-illuminated mice, whereas this thickness was significantly reduced in mice treated with free Ret-NH$_2$ under the same conditions.

Figure 19:
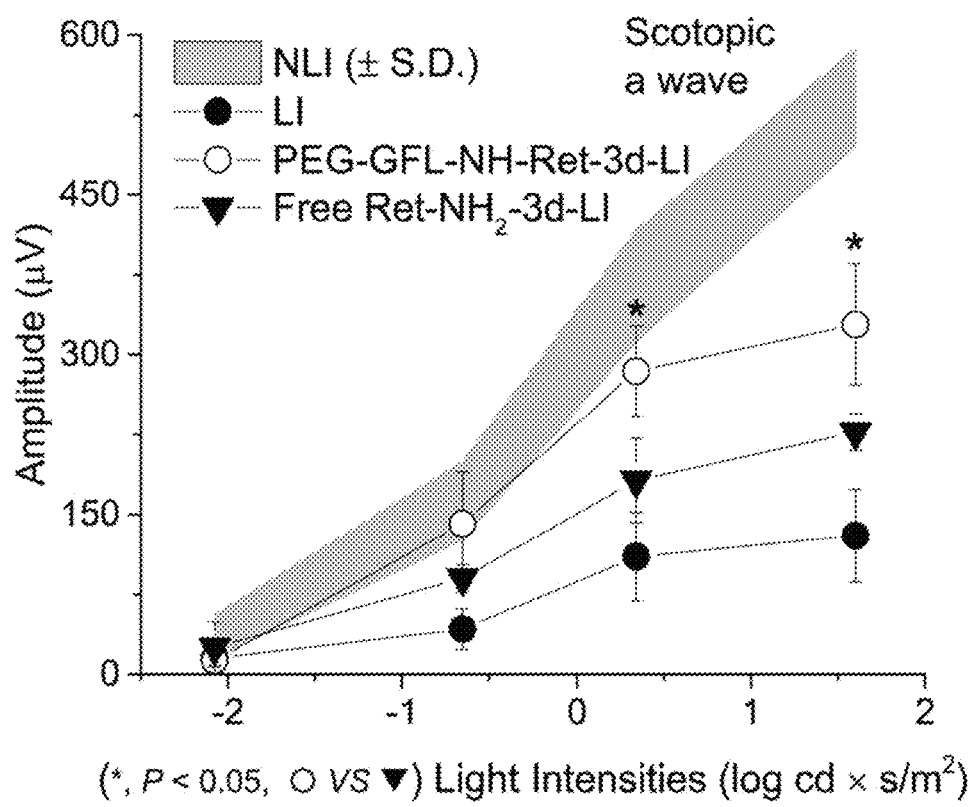
FIG. 19 illustrates a plot showing ERG evaluation of the effectiveness of PEG-GFL-NH-Ret on preserving retina function against light-induced acute retinal degeneration in 4-week-old Abca4$^{-/-}$Rdh8$^{-/-}$ mice.

Electroretinograms (ERGs) also were recorded to evaluate retinal function in these Abca4$^{-/-}$Rdh8$^{-/-}$ mice after treatment with free Ret-NH$_2$ or PEG-GFL-NH-Ret followed by strong light exposure three days later. ERG responses of mice treated with PEG-GFL-NH-Ret and light illumination (PEG-GFL-NH-Ret-3d-LI) were virtually the same as in mice with no light-illumination (NLI), but the ERG activity in mice with strong light illumination was substantially reduced and mice treated with free Ret-NH$_2$ also exhibited significant loss of ERG activity. The average ERG peak amplitudes of mice treated with the conjugate were significantly higher than those of mice treated with free Ret-NH$_2$ (FIG. 19).

Here we have demonstrated that oral administration of the polymer Ret-NH$_2$ conjugate, PEG-GFL-NH-Ret, provided more prolonged preservation of retinal structure and function against strong light exposure after a single oral dose than free Ret-NH$_2$ at an equivalent dose. Ret-NH$_2$ was previously shown to be effective in preserving visual cycle biochemistry and preventing light-induced retinal degeneration in animal models. Conjugation of the drug to biocompatible polymers resulted in more prolonged prevention of retinal degeneration against strong light exposure 3 days after oral administration. The duration of this effect was consistent with the transition time (72 h) of un-digested materials in the mouse GI tract. Because of its relatively high molecular weight (20 kDa), PEG cannot be absorbed in the intestine and the presence of the PEG conjugate in the gastrointestinal (GI) tract allows a gradual release of Ret-NH$_2$ through cleavage of the oligopeptide spacer by digestive peptidases in the small intestine and colon. As shown in the pharmacokinetics experiment, sustained drug release from the polymer drug conjugate in the GI tract can maintain minimally effective drug concentrations in the systemic circulation, which is critical to minimize any dose dependent toxic side effects of the drug. At the same time, a sufficient amount of Ret-NH$_2$ can still be delivered to the eye for prolonged periods, resulting in effective protection of the retina from strong light-induced degeneration.

Oral drug delivery is the most convenient drug delivery process. Prolonged retinal protection by the polymer drug conjugate can reduce dosing frequency and the overall dose, which also helps to minimize any potential dose-dependent toxicity and increase patient compliance. PEG-GFL-NH-Ret has clearly shown several advantageous features over free Ret-NH$_2$ for oral drug delivery, including sustained drug delivery, controlled pharmacokinetics, low drug concentrations in the systemic circulation and prolonged effective protection against light-induced retinal degeneration. Promising results from these experiments have demonstrated that PEG-GFL-NH-Ret conjugate can be used to effectively treat human retinal degenerative diseases, including Stargardt disease and age-related macular degeneration.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, we claim:

1. A method of treating an ocular disorder in a subject in need thereof, the method comprising:
    enterally administering to the subject a pharmaceutical composition comprising a retinylamine derivative polymer conjugate that includes a biocompatible polymer having a plurality of functional side chains and up to 4 retinylamine derivatives each linked to separate functional side chains of the biocompatible polymer with oligopeptide spacers, wherein each oligopeptide spacer is linked to a primary amine of the retinylamine derivative via an amide bond, the oligopeptide spacers being degradable by intestinal enzymes during digestion of the composition to provide delayed, and/or sustained delivery of the retinylamine derivatives to the eye upon enteral administration of the composition to a subject, each of the retinylamine derivatives having the following formula:

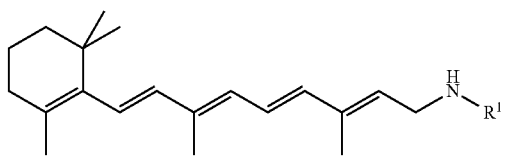

where R$^1$ is an amino acid residue, or a dipeptide that is linked to retinylamine by an amide bond, wherein R$^1$ is selected from the group consisting of glycine, L-valine-glycine, and glycine-L-valine, wherein the ocular disorder is light-induced retinal degeneration.

2. The method of claim 1, wherein the oligopeptide spacer is glycine-phenylalanine-leucine.

3. The method of claim 1, wherein the biocompatible polymer comprises polyethylene glycol.

4. The method of claim 3, wherein the polyethylene glycol has an average molecular weight of at least 4 kDa.

5. The method of claim 3, the polyethylene glycol including 8 propionic side chains.

6. The method of claim 1, wherein the pharmaceutical composition is administered to the subject orally.

* * * * *